(12) United States Patent
Murphy

(10) Patent No.: US 12,728,102 B2
(45) Date of Patent: Sep. 8, 2026

(54) TRANSDERMAL PATCH OF A PORTABLE ULTRASOUND-GENERATING SYSTEM FOR IMPROVED DELIVERY OF THERAPEUTIC AGENTS AND ASSOCIATED METHODS OF TREATMENT

(71) Applicant: NanoVibronix, Inc., Elmsford, NY (US)

(72) Inventor: Brian Murphy, St. Charles, IL (US)

(73) Assignee: NanoVibronix, Inc., Elmsford, NY (US)

(*) Notice: Subject to any disclaimer, the term of this patent is extended or adjusted under 35 U.S.C. 154(b) by 493 days.

(21) Appl. No.: 17/025,969

(22) Filed: Sep. 18, 2020

(65) Prior Publication Data

US 2022/0087948 A1 Mar. 24, 2022

(51) Int. Cl.
*A61K 9/70* (2006.01)
*A61B 8/00* (2006.01)
(Continued)

(52) U.S. Cl.
CPC .......... *A61K 9/7084* (2013.01); *A61K 9/0009* (2013.01); *A61K 9/7038* (2013.01); *A61K 9/7046* (2013.01); *A61K 9/7053* (2013.01); *A61K 9/7061* (2013.01); *A61K 9/7069* (2013.01); *A61K 9/7092* (2013.01); *A61K 31/658* (2023.05); *A61K 36/3482* (2024.05); *A61K 45/06* (2013.01); *A61M 31/002* (2013.01); *A61M 37/0092* (2013.01); *A61P 17/02* (2018.01); *A61P 29/00* (2018.01); *A61B 8/4236* (2013.01); *A61B 8/4281* (2013.01);
(Continued)

(58) Field of Classification Search
None
See application file for complete search history.

(56) References Cited

U.S. PATENT DOCUMENTS 3,427,481 A 2/1969 Lenahan
4,040,414 A 8/1977 Suroff
(Continued)

FOREIGN PATENT DOCUMENTS

AU 1672492 A 12/1992
CA 2125167 A1 6/1993
(Continued)

OTHER PUBLICATIONS

Sanni et al ("Powering low-power implants using PZT transducer discs operated in the radial mode", Smart Materials and Structure, vol. 22 (2013), 115005 (12 pages)). (Year: 2013).*
(Continued)

*Primary Examiner* — Sin J Lee
(74) *Attorney, Agent, or Firm* — The Roy Gross Law Firm, LLC; Roy D. Gross

(57) ABSTRACT

A portable surface acoustic wave (SAW)-generating system, a transdermal patch, and methods of treatment with improved transdermal administration of drugs are provided. Application of the transdermal patch comprising a therapeutically effective amount of the *cannabis* id, such as a *cannabis* drug, to the skin in combination with SAW results in a synergistic effect on delivery and absorption of the at least one drug as compared to topical administration of the drug via the transdermal patch without the surface acoustic waves generated by the portable SAW-generating system.

14 Claims, 13 Drawing Sheets

(51) Int. Cl.

| | |
|---|---|
| *A61K 9/00* | (2006.01) |
| *A61K 31/00* | (2006.01) |
| *A61K 36/185* | (2006.01) |
| *A61K 45/06* | (2006.01) |
| *A61M 31/00* | (2006.01) |
| *A61M 37/00* | (2006.01) |
| *A61P 1/00* | (2006.01) |
| *A61P 17/02* | (2006.01) |
| *A61P 29/00* | (2006.01) |

(52) U.S. Cl.
CPC .... *A61B 8/4427* (2013.01); *A61M 2037/0007* (2013.01); *A61P 1/00* (2018.01)

(56) References Cited

U.S. PATENT DOCUMENTS

| | | | | |
|---|---|---|---|---|
| 4,419,248 | A | 12/1983 | Costerton | |
| 4,511,563 | A | 4/1985 | Schmolka | |
| 4,767,619 | A | 8/1988 | Murray | |
| 4,861,760 | A | 8/1989 | Mazuel | |
| 4,883,660 | A | 11/1989 | Blackman | |
| 5,053,227 | A | 10/1991 | Chiang | |
| 5,059,426 | A | 10/1991 | Chiang | |
| 5,200,665 | A | 4/1993 | Iijima | |
| 5,229,130 | A | 7/1993 | Sharma | |
| 5,318,780 | A | 6/1994 | Viegas | |
| 5,636,180 | A | 6/1997 | Grothaus | |
| 5,876,602 | A | 3/1999 | Jons | |
| 5,895,362 | A | 4/1999 | Elstrom | |
| 5,954,977 | A | 9/1999 | Miller | |
| 6,004,438 | A | 12/1999 | Woodson | |
| 6,096,225 | A | 8/2000 | Yang | |
| 6,156,549 | A | 12/2000 | Drewes | |
| 6,328,992 | B1 * | 12/2001 | Brooke | A61K 9/7061 424/443 |
| 6,426,491 | B2 | 7/2002 | Naya | |
| 6,428,477 | B1 | 8/2002 | Mason | |
| 6,433,244 | B1 | 8/2002 | Roe | |
| 6,630,507 | B1 | 10/2003 | Hampson | |
| 6,864,852 | B2 | 3/2005 | Chiang | |
| 6,953,341 | B2 | 10/2005 | Black | |
| 7,165,451 | B1 | 1/2007 | Brooks | |
| 7,393,501 | B2 | 7/2008 | Zumeris | |
| 7,429,248 | B1 | 9/2008 | Winder | |
| 7,789,876 | B2 | 9/2010 | Zikorus | |
| 7,955,262 | B2 | 6/2011 | Rosenberg | |
| 8,287,483 | B2 | 10/2012 | Mitragotri | |
| 9,492,687 | B2 | 11/2016 | Lewis | |
| 2002/0055702 | A1 | 5/2002 | Atala | |
| 2002/0068866 | A1 | 6/2002 | Zikorus | |
| 2003/0083599 | A1 | 5/2003 | Kitov | |
| 2003/0177819 | A1 | 9/2003 | Maale | |
| 2003/0236487 | A1 | 12/2003 | Knowlton | |
| 2004/0027034 | A1 | 2/2004 | Kawaguchi | |
| 2004/0073267 | A1 | 4/2004 | Holzer | |
| 2004/0236268 | A1 | 11/2004 | Mitragotri | |
| 2004/0236269 | A1 | 11/2004 | Marchitto | |
| 2005/0038376 | A1 | 2/2005 | Zumeris | |
| 2005/0075599 | A1 | 4/2005 | Redding | |
| 2005/0095351 | A1 | 5/2005 | Zumeris | |
| 2005/0137656 | A1 | 6/2005 | Malak | |
| 2005/0200434 | A1 | 9/2005 | Takano | |
| 2005/0267451 | A1 | 12/2005 | Black | |
| 2005/0268921 | A1 | 12/2005 | Zumeris | |
| 2005/0283110 | A1 | 12/2005 | Atala | |
| 2006/0184071 | A1 | 8/2006 | Klopotek | |
| 2007/0038156 | A1 | 2/2007 | Rosenberg | |
| 2007/0232962 | A1 * | 10/2007 | Zumeris | A61L 2/025 601/2 |
| 2008/0112895 | A1 | 5/2008 | Kottayil | |
| 2009/0142390 | A1 * | 6/2009 | Jackson | A61K 9/7061 514/170 |
| 2011/0129521 | A1 * | 6/2011 | Epner | A61P 35/00 424/449 |
| 2012/0277640 | A1 * | 11/2012 | Lewis, Jr. | A61B 8/4281 601/2 |
| 2013/0230609 | A1 * | 9/2013 | Modak | A61P 17/10 424/769 |
| 2018/0311181 | A1 * | 11/2018 | Kochinke | A61K 45/06 |
| 2019/0175956 | A1 * | 6/2019 | Dolezal | A61K 8/99 |

FOREIGN PATENT DOCUMENTS

| | | | | |
|---|---|---|---|---|
| CA | 2545798 | A1 | 9/2004 | |
| EP | 0680337 | A4 | 7/1997 | |
| EP | 1186298 | B1 * | 12/2005 | A61K 31/352 |
| IL | 131623 | | 1/2001 | |
| JP | 2788307 | B2 | 8/1998 | |
| JP | 3118251 | B2 | 12/2000 | |
| JP | 2003170172 | A | 6/2003 | |
| JP | 2005303980 | A | 10/2005 | |
| JP | 3734341 | B2 | 1/2006 | |
| JP | 4447250 | B2 | 4/2010 | |
| RU | 2419395 | C2 | 5/2011 | |
| WO | WO-95/05137 | A1 | 2/1995 | |
| WO | WO-98/55605 | A1 | 12/1998 | |
| WO | WO-03/099100 | A2 | 12/2003 | |
| WO | WO-2005/117156 | A2 | 12/2005 | |

OTHER PUBLICATIONS

Allen et al., "Drug Delivery Systems: Entering the Mainstream," Science 303:1818-22 (2004).

Allen et al., "Liposomal Drug Delivery Systems, From Concept to Clinical Applications," Adv. Drug Deliv. Rev. 65:36-48 (2013).

De Vries et al., "Dronabinol and chronic pain: Importance of mechanistic considerations," Expert Opin. Pharmacother. 15:1525-34 (2014).

Finnerup et al., "The evidence for pharmaco-logical treatment of neuropathic pain," Pain 150:573-81 (2010).

Grotenhermen F., "Pharmacokinetics and pharmacodynamics of cannabinoids," Clin. Pharmacokinet. 42:327-60 (2003).

Guindon et al., "The endocannabinoid system and pain," CNS Neural. Disord. Drug Targets 8:403-21 (2009).

Information Disclosure Statement for U.S. Pat. No. 9,028,748.

Information Disclosure Statement for U.S. Pat. No. 9,585,977.

International Preliminary Report on Patentability issued on Aug. 26, 2008 for PCT/US2007/004842.

International Preliminary Report on Patentability issued on Aug. 26, 2008 for PCT/US2007/004849.

International Search Report for PCT/US2007/004842.

International Search Report for PCT/US2007/004849.

Jensen et al., "Medical marijuana and chronic pain: A review of basis science and clinical evidence," Current Pain Headache Rep., 119 (2018).

Jensen et al., "The impact of neuropathic pain on health-related quality of life: Review and implications," Neurology 68:1178-82 (2007).

Kumari et al., "Biodegradable polymeric nan-oparticles based drug delivery systems," Colloids Surf Biointerfaces 75:1-18 (2010).

Miyasaka et al; "Ultrasonic Tissue Characterization of Photodamaged Skin by Scanning Acoustic Microscopy" Tokai J Exp Clin Med vol. 30, No. 4, pp. 217-225, 2005.

Pacifici R et al., "Evaluation of Long-term stability of cannabinoids in standardized preparations of cannabis flowering tops and cannabis oil by ultra-high- performance liquid chromatography tandem mass spec-trometry," Clin. Chem. Lab. Med. 56:e94-e96 (2018).

Stucky et al., "Mechanisms of pain," Proc. Natl. Acad. Sci. USA 98:11845-6 (2011).

Uhoda et al; Effect of haemodialysis on acoustic shear wave propagation in the skin; Dermatology 2004, 209(2): 95-100.

Zhang et al., "Can modulating inflannnatory response be a good strategy to treat neuropathic pain?" Curr. Pharm. Des. 21:831-9 (2015).

* cited by examiner 330
650
750
610
400, 500
620
610
600

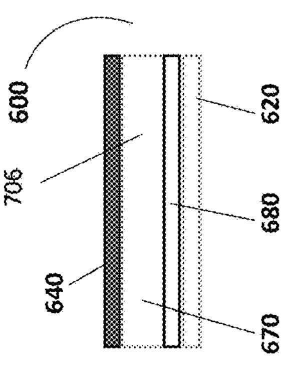
FIG. 7D
Matrix Systems
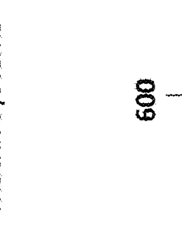
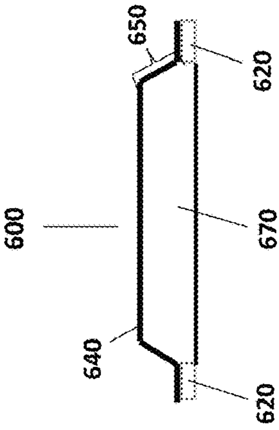
FIG. 7C
FIG. 7B
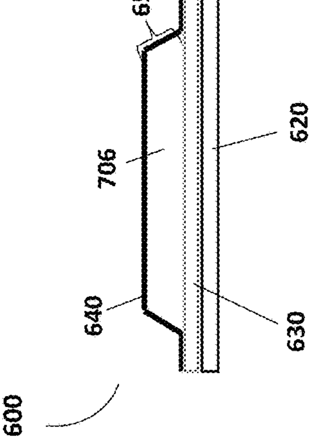
FIG. 7A

TRANSDERMAL PATCH OF A PORTABLE ULTRASOUND-GENERATING SYSTEM FOR IMPROVED DELIVERY OF THERAPEUTIC AGENTS AND ASSOCIATED METHODS OF TREATMENT

INCORPORATION BY REFERENCE

The contents of U.S. patent application Ser. No. 11/710,615 (issued as U.S. Pat. No. 9,585,977) are hereby incorporated by reference herein in their entirety. Also incorporated by reference herein are additional patent publications specifically referenced as such in the following description.

FIELD OF INVENTION

Embodiments of the present invention relate to methods and devices for creating surface acoustic waves on human skin surfaces for therapeutic, wound-healing, disinfecting, and pain management applications. The methods and devices of the invention are suitable for use in transdermal administration of therapeutic agents, and to the administration of therapeutically effective dosages of various drug products, including, but not limited to, *cannabis* products.

BACKGROUND

While benefits of cannabis, or *Cannabis sativa*, for treating symptoms of diverse neurologic and psychiatric conditions have been recognized and practiced by ancient civilizations dating back to 4000 B.C., the psychoactive effects of cannabis have also led to abuse and it becoming labeled as a "gateway drug" for more additive compounds. In the present day, there is no class of therapeutic compounds subject to more controversy and stigma than cannabis and so-called "cannabinoids"—the active components *C. sativa.*

Despite the legal and social barriers preventing its widespread use, the use of cannabinoids to various illnesses remains of great interest to the medical community, as medical uses have been found for active ingredients of cannabis, including the ingredients tetrahydrocannabinol (THC), cannabinol (CBN), cannabidiol (CBD) and cannabichromene (CBC). While cannabis remains defined under U.S. federal law as having no medical use, it is worthy of note that U.S. Pat. No. 6,630,507 is held by the United States Department of Health and Human Services, covering the use of cannabinoids for treating a wide range of diseases. Specifically, there is a growing body of evidence to suggest that cannabinoids are beneficial for a range of clinical conditions, including in particular pain, inflammation, epilepsy, sleep disorders, and the symptoms of multiple sclerosis, anorexia, schizophrenia, cancer, and other conditions.

While more than 100 different cannabinoids can be isolated from *C. sativa*, the primary psychoactive compound is tetrahydrocannabinol (THC). However, adverse psychoactive events can be caused by THC, depending on dosage and previous patient tolerance. Unlike THC, CBD, which is the major non-psychoactive phytocannabinoid component of *C. sativa*, has been found to have little affinity for cannabinoid receptors CB1 and CB2, which are part of one of the important endogenous lipid signaling pathways, named the "endocannabinoid system."

Cannabinoids are highly lipophilic molecules (log P 6-7) with very low aqueous solubility (2-10 Ug/mL) (see Reference 1) that are susceptible to degradation, especially in solution, via the action of light and temperature as well as via auto-oxidation (see Reference 2). Proper formulation can therefore play a crucial role in increasing solubility and physicochemical stability of cannabinoids. Various administration and delivery forms have been tested for therapeutic use, most commonly either by inhalation or oral administration. The pharmacokinetics and dynamics of cannabinoids vary as a function of the route of administration, with absorption showing the most variability of the principal pharmacokinetic steps. Specifically, absorption of cannabinoids is affected both by intrinsic product lipophilicity and by inherent organ tissue differences (i.e., alveolar, dermal, gastric).

THC, for example, is effective in vivo at very low doses but is rapidly metabolized in the body such that concentration levels of the chemical in the bloodstream decrease rapidly if administered through traditional methods. Attempts have been made to orally administer the cannabinoid $\Delta^9$-THC (Dronabinol) in the form of a capsule, but severely nauseated patients are often not able to retain the capsule in their stomachs long enough for the drug to take effect, and this problem becomes compounded when patients must take four to six doses around chemotherapy. Another issue with capsules in general, as with smoked marijuana, is that patients absorb the drug relatively rapidly and therefore receive high drug concentrations in their body. It is these high drug concentrations, or peak levels, that are often associated with psychoactive and other central nervous system side effects. Due to its high lipophilicity, THC exhibits a strong tendency to bind to tissue and protein, thus making transdermal application difficult. However, transdermal administration allows for smaller dosages of THC to be administered over an extended period of time, thereby allowing the concentration levels of the chemical to remain relatively steady in the bloodstream.

In view of the above, there is a long-felt need in the art for cannabinoids to be delivered transdermally (across the skin). Preferably, cannabinoids will be delivered in a topical composition or in a transdermal patch or the like, and a therapeutically effective dose of the cannabinoid(s) or other drug(s) will be released in a controlled manner over time. There is also a need to transdermally deliver, in a controlled manner, drugs and topical formulations other than just cannabinoids to treat various illnesses and/or symptoms.

SUMMARY

The present invention overcomes problems associated with existing drug delivery systems and, more specifically, expands on methods and devices for the transdermal administration of therapeutic agents, such as cannabis products, by the improved methods comprising applying ultrasound waves to and in combination with the transdermal patches described herein.

In one aspect of the invention, compositions comprising at least one cannabinoid or derivatives thereof are provided for treatment of various conditions. Specifically, in embodiments of the present invention, a pharmaceutical composition comprises a therapeutically effective amount of, or an extract consisting essentially of a therapeutically effective amount of at least one cannabinoid selected from the group consisting of cannabidiol (CBD) or a derivative thereof, tetrahydrocannabinol (THC) or a derivative thereof, and any combination thereof for treatment of various disorders and conditions. According to embodiments of the invention, the pharmaceutical composition is preferably administered in a route selected from topical, transdermal, and combinations thereof. In additional embodiments of the invention, the pharmaceutical composition is formulated in a form selected from the group consisting of a cream, ointment, lotion, foam, film gel, liquid, and any combinations thereof. It is also within the scope of the invention to provide the pharmaceutical composition as described herein, wherein the composition is administered in combination with an additional therapeutic agent.

In a second aspect of the invention, cannabinoids are delivered topically or transdermally to a patient to alleviate the harmful side effects and/or avoid quick metabolism of the cannabinoids. Preferably, the cannabinoids are delivered via a transdermal patch. In specific embodiments, the invention provides a method for treating a subject with a transdermal cannabis preparation, which is most conveniently accomplished by application of the transdermal structure or "patch" described herein.

In a third aspect, the invention provides a skin patch or related assembly of materials, preferably a transdermal patch, configured to contain and selectively administer an effective amount of a therapeutic agent or drug, preferably comprising at least one cannabinoid, during a predetermined period of time. In preferred embodiments, the transdermal patch contains and effectively administers an effective amount of cannabis or its chemical constituents to a patient. An object of the transdermal patch according to the present invention is to allow for controlled delivery of the therapeutic agent or drug, or more specifically cannabinoids, such that plasma levels of the chemicals may be controlled in a safe, convenient and effective manner for the subject receiving treatment.

In embodiments, the transdermal patch includes a reservoir for retaining and dispersing the therapeutic agent or drug. In preferred embodiments the reservoir is configured to retain and disperse the active ingredients of a cannabis formulation. In certain embodiments, the reservoir includes a rate controlling means that regulates flux or diffusion flow rate of the therapeutic agent or drug to the skin. The rate controlling means may comprise a nonporous polymer membrane for regulating the flux, or a porous material made of materials suitable for controlling the diffusion rate of the therapeutic agent or drug. The reservoir means may also comprise a polymer matrix material which suspends the therapeutic agent or drug, or the cannabis, and releases it in a controlled manner. The flux of the polymer matrix material may further be regulated by a rate controlling membrane.

Specifically provided is a transdermal patch, comprising: an adhesive layer disposed over at least a portion of an external lower surface of the transdermal patch; a protective layer removably disposed over the adhesive layer; an impermeable layer forming an outer protective backing of the transdermal patch; a rate-controlling microporous membrane, wherein the impermeable layer and the rate-controlling microporous membrane define a cavity therebetween in an interior of the transdermal patch; and a therapeutically effective amount of at least one *cannabis* drug disposed within the cavity, wherein: the at least one *cannabis* drug is not psychoactive and is a cannabinoid selected from the group consisting of tetrahydrocannabinol (THC), cannabinol (CB), cannabidiol (CBD), and cannabichromene (CBC); and the at least one *cannabis* drug is contained in an amount that is therapeutically effective for treating or alleviating symptoms of a disease or condition of a subject.

In embodiments, the transdermal patch further comprises an actuator with an integrated piezo transducer located on a lower surface of the transdermal patch such that a metal surface of the transducer faces a direction of adhesion of the transdermal patch, wherein the transducer has a low profile height of 6 mm or less.

In embodiments, the therapeutically effective amount of the at least one *cannabis* drug is comprised in a pharmaceutical composition, the pharmaceutical composition further comprising one or more pharmaceutically acceptable excipient(s) to create a transdermal dosage form selected from the group consisting of a gel, ointment, paste, cream, lotion, and suspension. Preferably, the pharmaceutical composition comprises a therapeutically effective amount of CBD as the at least one *cannabis* drug, and at least one permeation enhancer. In some embodiments, the pharmaceutical composition further comprises an analgesic or another drug effective for treating or alleviating the symptoms of a disease or condition of a subject. In certain embodiments, the pharmaceutical composition comprises at least one analgesic or drug effective for alleviating pain.

In embodiments, the transdermal patch may comprise two or more polymeric matrix layers respectively disposed over two or more rate-controlling microporous membranes, wherein a first polymeric matrix layer comprises a therapeutically effective amount of the at least one *cannabis* drug, and a second polymeric matrix layer comprises a therapeutically effective amount of at least one drug different from the at least one *cannabis* drug in the first polymeric matrix layer. In such embodiments, the first polymeric matrix layer may comprise a therapeutically effective amount of CBD and the second polymeric matrix layer may comprise a therapeutically effective amount of at least one analgesic and/or anti-inflammatory agent.

A fourth aspect of the invention provides for improved transdermal absorption of a therapeutic agent by concurrent application of ultrasonic waves. In embodiments, improved transdermal absorption of a therapeutic agent is achieved by application of ultrasonic waves to the transdermal patch of the invention, said transdermal patch containing the therapeutic agent. In certain embodiments, the therapeutic agent comprises a drug.

For use in embodiments of the invention, provided is a portable surface acoustic wave (SAW) generating system, comprising: an energy generating module configured to generate a driving signal when in an active state, the energy generating module comprising: a power source, a controller, an oscillator, and a processor; and an actuator comprising a piezo-ultrasound transducer incorporated into a transdermal patch of and coupled to the energy generating module, wherein the ultrasound transducer is configured to receive the driving signal from the energy generating module, to transform the driving signal into ultrasonic energy, and to control a direction of the ultrasonic energy emitted from the ultrasound transducer, wherein the ultrasound transducer is incorporated into the transdermal patch.

In preferred embodiments, the transdermal patch is configured so as to provide a pocket or holding compartment for an ultrasound transducer of the portable SAW-generating system such that a metal surface of the transducer faces, and is incorporated into, the adhesive external surface of the transdermal patch. That is, upon removal of a removable protective layer, the transdermal patch can be applied to a skin surface of a subject with the transducer being in direct contact with the skin. In such embodiments, a reservoir of the transdermal patch comprising an effective amount of at least one drug is preferably incorporated in a position next to or in close proximity to the location of the transducer, such that upon activation of the transducer, the ultrasonic waves help facilitate permeation of the drug through a microporous permeable membrane or a drug-in-adhesive matrix onto the skin surface, and transdermal absorption of the drug through the skin.

In additional embodiments, the invention provides for methods of treating or alleviating symptoms associated with a disease or condition in a subject, comprising: removing the protective layer from the transdermal patch to reveal the adhesive layer; topically applying the transdermal patch to a skin surface of the subject; and activating an energy generating module or unit connected to the actuator in the transdermal patch, causing the actuator to vibrate in a selected vibration mode and the transducer to produce surface acoustic waves on the skin surface around the transdermal patch.

In embodiments, two or more transdermal patches may be applied to the skin surface, each being connected to a separate processor or to the same processor. In specific embodiments, the method of the invention treats or alleviates symptoms associated with a disease or condition of the subject selected from the group consisting of arthritis, neurodegenerative diseases, anxiety, AIDS, and cancer. Embodiments of the method are also especially effective for treatment of chronic and/or acute pain in a subject. In such embodiments, the transdermal patch may further comprise at least one additional drug suitable for treatment of pain such that application of the transdermal patch and the surface acoustic waves to the skin surface results in administration and transdermal absorption of the therapeutically effective amount of CBD and a therapeutically effective amount of the at least one additional drug for treatment or alleviation of acute or chronic pain of the subject.

In still other embodiments, provided are improved methods for transdermally administering a drug through a skin surface of a subject, comprising: applying to the skin surface of the subject a transdermal patch comprising a pharmaceutical composition which comprises: a therapeutically effective amount of a cannabinoid; a permeation enhancer; a pharmaceutically acceptable excipient, such as a carrier; and optionally one or more additional cannabinoid or a drug effective for treatment of a disease or condition of the subject; and activating a portable SAW-generating system to apply surface acoustic waves to the skin surface of the subject surrounding the transdermal patch, the surface acoustic waves being applied through a transducer incorporated in the transdermal patch and electronically coupled to the portable SAW-generating system, wherein the application of the transdermal patch comprising the pharmaceutical composition together with the application of the surface acoustic waves to the skin surface results in synergistic effect on delivery and absorption of the at least one drug as compared to topical administration of the drug alone, including in the transdermal patch, without the surface acoustic waves generated by the portable SAW-generating system.

In still further embodiments, an object of the present invention is to solve problems described herein and other problems that are not specifically discussed, which would nevertheless be discoverable by a skilled artisan.

BRIEF DESCRIPTION OF THE DRAWINGS

The above and further advantages of the present invention may be better understood by referring to the following description in conjunction with the accompanying figures.

It will be appreciated that, for simplicity and clarity of illustration, elements shown in the drawings have not necessarily been drawn accurately or to scale. For example, the dimensions of some elements may be exaggerated relative to other elements for clarity or several physical components may be included in one functional block or elements. Further, where considered appropriate, reference numerals may be repeated among the drawings to indicate corresponding or analogous elements.

FIG. 7A-7D are cross-sectional illustrations of different configurations of the transdermal patch according to embodiments of the invention. FIG. 7A shows a simple reservoir system, FIG. 7B shows a single-layer drug-in-adhesive matrix system, FIG. 7C shows a simple matrix system, and FIG. 7D shows a multi-layer polymeric matrix system.

FIGS. 8A-8C are schematic illustrations of a transdermal patch on a skin surface, wherein FIG. 8A shows a pre-activation configuration, FIG. 8B shows generation of SAW from the actuator to the at least one drug comprised in the reservoir, and FIG. 8C shows drug delivery from the reservoir to the skin coupled with SAW.

DETAILED DESCRIPTION OF THE DRAWINGS

I. Definitions

Figure 1:
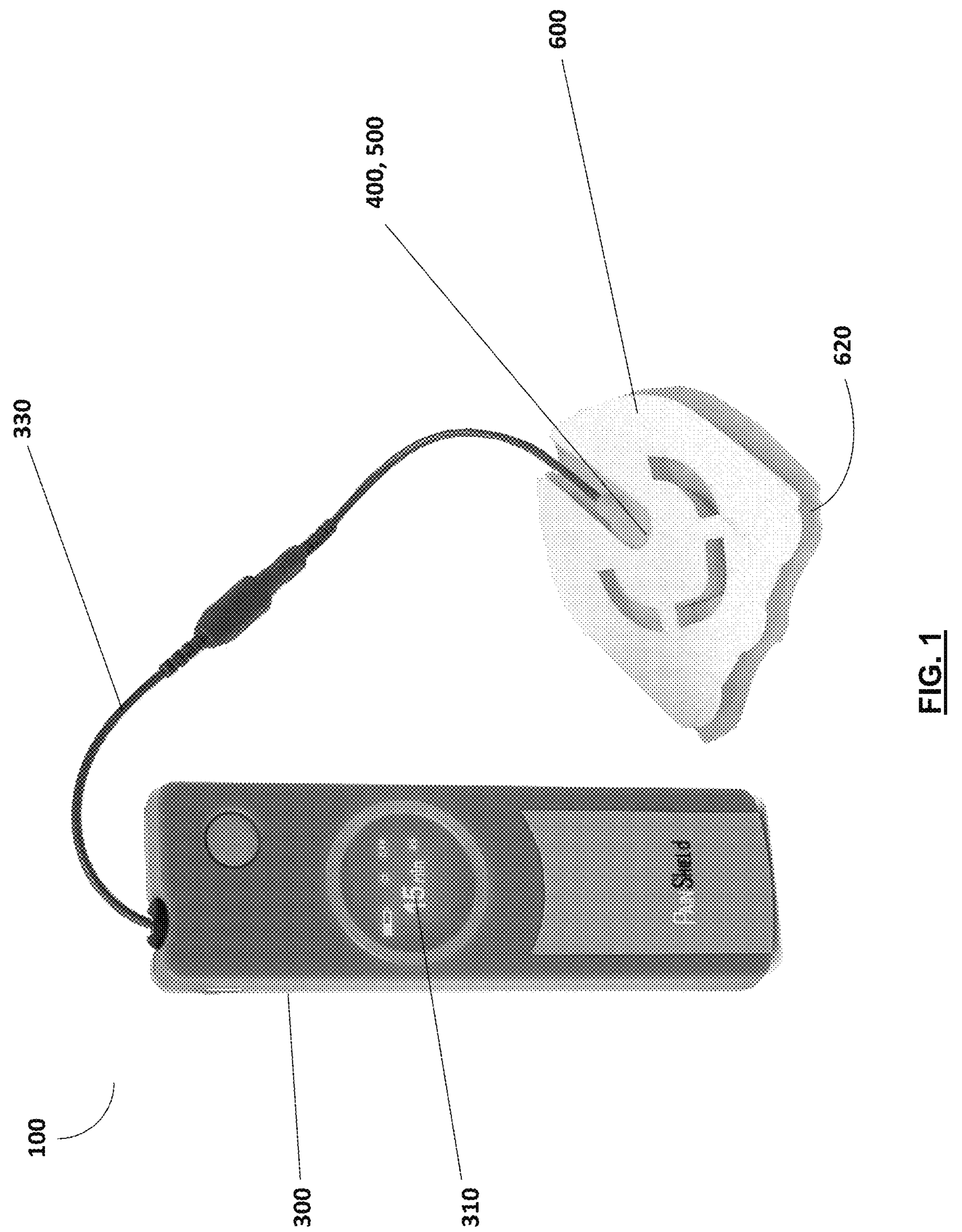
FIG. 1 is an illustration of a SAW-based system that includes, inter alia, a portable ultrasonic device (energy generating module or unit) connected to an actuator within a transdermal patch according to an embodiment of the invention.

The term "cannabinoid" as used herein is meant to include a class of diverse chemical compounds that act on cannabinoid receptors on cells that repress neurotransmitter release in the brain, as well as various cannabinoid analogs and their pharmaceutically acceptable salts, solvates, metabolites, and metabolic precursors. The receptor proteins include the endocannabinoids (produced naturally in the body by humans and animals), the phytocannabinoids (found in and some other plants), and synthetic cannabinoids.

The term "cannabidiol" (or "CBD") refers to one of at least 85 active cannabinoids identified in *cannabis*. Cannabidiol is a major phytocannabinoid, accounting for up to 40% of the plant's extracts. CBD has little activity at cannabinoid type 1 receptors (CB1) but greater activity at the cannabinoid type 2 receptors (CB2), and is a non-competitive CB1/CB2 receptor antagonist. CBD may increase the potency of THC's effects by increasing CB1 receptor density or through another CB1-related mechanism, while also being an inverse agonist of CB2 receptors. It possesses anti-inflammatory, antiproliferative and pro-apoptotic effects, inhibits cancer cell migration, adhesion and invasion, and is considered to be the "medical component" of and hemp. CBD acts as serotonin (5-HT1A) receptor agonist, which may explain its antidepressant, anxiolytic and neuroprotective effects. It also modulates opioid receptors involved with pain perception. Furthermore, CBD is not psychoactive and has been found to relieve convulsions, inflammation, anxiety, and nausea.

The term "tetrahydrocannabinol" (or "THC") refers to the principal psychoactive constituent (or cannabinoid) of the plant. It has a partial agonist activity at the cannabinoid receptor CB1 and the cannabinoid receptor CB2.

"Metabolic precursors" as used herein in connection with cannabinoids are meant to include prodrugs and other materials that are metabolized in the subject's body (cutaneously or systemically, or both) to a cannabinoid or an active cannabinoid mimetic. Suitable metabolic precursors include those that are less lipophilic (i.e., more water-soluble) relative to the cannabinoid into which they are metabolized. Examples of such metabolic precursors include those described in, for example U.S. Pat. No. 5,847,128 to Martin et al., which is hereby incorporated by reference herein.

"Metabolites" as used herein, are meant to include compounds which are produced by the metabolic processes (e.g., cutaneous metabolic processes and/or systemic metabolic processes) of the subject's body. Suitable metabolites can be identified, for example, by studying the kinetids of drug enzymatic metabolism in skin homogenates. Suitable metabolites can be identified, for example, by studying the kinetics of drug enzymatic metabolism in skin homogenates. Illustratively, skin homogenates can be prepared from 250 m DERMATOMED fresh healthy abdominal plastic surgery samples. The skin is homogenized in 4-(2-hydroxyethyl)-1-piperazineethane-sulfonic acid ("HEPES")-buffered Hanks' balanced salt solution. Whole homogenates can be used for these studies or, if significant mitochondrial or nuclear metabolism is found not to occur (e.g., by comparing the degree of metabolism in the supernatant to the degree of metabolism in the whole homogenate), the studies can be carried out on only the supernatant fraction. The drug (solubilized in, e.g., buffer, ethanol dimethylsulfoxide, or combinations thereof) is then incubated with the homogenate (r supernatant) along with NADPH (or a generating system), NADH, $MgCl_2$, and bovine serum albumin. The total volume of ethanol in the reaction mixture should be small (e.g., under 2%) to help minimize ethanol's detrimental effects on the enzymes. After incubating for a period of time, the reaction is terminated with 15% trichloroacetic acid, and the drug and its metabolites are obtained by solid-phase extraction. The metabolite or metabolites formed can then be identified and assayed by any suitable method (e.g., HPLC).

"Enhancer" as used herein is meant to encompass any enhancer or combination of enhancers that increases the flux of a substance across the stratum corneum.

"Carrier" or "vehicle" as used herein refer to carrier materials suitable for transdermal drug administration, and include any such materials known in the art, e.g., any liquid, gel, emulsion, solvent, liquid diluent, solubilizer, or the like, which is nontoxic and which does not interact with other components of the composition in a deleterious manner. The term "carrier" or "Vehicle" as used herein may also refer to stabilizers, crystallization inhibitors, dispersing agents or other types of additives useful for facilitating transdermal drug delivery. It will be appreciated that compounds classified as "vehicles" or "carriers" may sometimes act as permeation enhancers, and vice versa, and, accordingly, these two classes of chemical compounds or compositions may sometimes overlap.

The term "nonpsychoactive" as used herein means not having an effect on the mind or mental processes.

The term "relieve" as used herein is meant to include complete elimination as well as any clinically or quantitatively measurable reduction in a subject's symptoms and/or discomfort.

The term "oil" as used herein comprises any one or a mixture of pharmaceutical grade light mineral oils, vegetable oils, fish and animal oils. Examples of vegetable oils include sesame, corn, cottonseed, almond, orange, lemon, eucalyptus, olive, peanut, sunflower, cinnamon, clove and soybean oils. Other suitable oils include cod liver and castor oils.

The term "topical formulation" as used herein may be selected from the group consisting of a cream, a lotion, a paste, a gel, and a liquid pharmaceutical compositions, which releases one or more therapeutic agents or drugs (e.g., cannabinoid drug(s)) at a predetermined rate over a defined period of time to a defined site of application. For purposes of the present disclosure, "topical formulation" refers to the final formulation containing the base formulation or the base formulation in combination with effective amount(s) of therapeutic or active agent(s). In certain embodiments, the therapeutic agent includes at least one of CBD. In preferred embodiments, the topical formulation is "ready to use" or a stock formulation containing effective amount(s) of the therapeutic agent(s) required to perform the desired effect.

As used herein, "transdermal" delivery is the delivery by passage of a therapeutic agent or drug (e.g., cannabinoid drug) through the skin and into the bloodstream.

The term "transdermal therapeutic system" is defined as a drug-containing patch of the invention which releases one or more drugs at a predetermined rate over a defined period of time to a defined site of application.

As used herein, a "therapeutically effective" or "effective" means a nontoxic but sufficient amount of at least one cannabinoid compound(s) to provide the desired therapeutic effect.

The terms "carrier formulation" or "base formulation" refers to a control formulation containing inactive ingredients. The base formulation was used as a control in the experiments described herein. The base formulation was also used to produce combinations with reselected ingredients in order to test synergistic effects of the combination as compared to each of the ingredients alone or their piratical combinations.

The term "surface acoustic waves" (SAW) includes several types of waves or combinations of waves, including: Surface-Rayleigh (elliptical orbit, symmetrical mode; Plate Wave-Lamb (perpendicular to surface; extensional wave);

Plate Wave-Love (parallel to plane layer, perpendicular to wave direction); Stoneley or Leaky Rayleigh Wave (guided along interface); and Sezawa (anti-symmetrical mode). Surface or Rayleigh waves travel along the boundary between two different media, penetrating to a depth of about one wavelength. The particle movement has an elliptical orbit. Lamb waves are a special type of Rayleigh waves, which occur when a material is particularly thin. In preferred embodiments, the present invention relates to methods of treatment and drug administration with SAW of Rayleigh, "pseudo" Rayleigh or Lamb-type waves.

The term "sustained release" in connection with a dosage form refers to the release of a drug at a predetermined rate in order to maintaining a constant drug concentration for a specific period of time with minimum side effects. This definition is more akin to a "controlled release" than "sustained."

The term "wound" as used in connection with "wound healing" includes ulcers, such as venous ulcers, burns, ulcerated wounds due to, e.g., diabetes, surgical incisions or other surgical cuttings including stitched surgical cuttings, skin grafts, hair transplants, revascularization, bed sores, tissue dehiscence, and ligament and tendon repair and reconstruction. In general, the term "wound healing" encompasses addressing or treating damage to, repair of, or restoration of soft tissue.

II. Pharmaceutical Composition

As discussed above, there is a growing body of evidence to suggest that cannabinoids are beneficial for a range of clinical conditions, including (without limitation) pain, inflammation, epilepsy, sleep disorders, anxiety, as well as the symptoms of multiple sclerosis, anorexia, schizophrenia and various other conditions. The transformation of cannabinoids from herbal preparations into highly regulated prescription drugs is therefore a rapidly progressing field.

Pain and inflammation are typically physiological responses to tissue injury, infection and genetic changes, which can be divided into two phases: acute and chronic. See Reference 3. The acute phase is the early, non-specific phase and is characterized by local vasodilation, increased capillary permeability, the accumulation of fluid and blood proteins in the interstitial spaces, the migration of neutrophils out of the capillaries, and the release of inflammatory mediators (e.g., cytokines, lymphokines and histamine). Pain is produced by all these pro-inflammatory agents that also lead to hyperalgesia through the activation of the corresponding receptors, which are expressed by nociceptive terminals. If a condition that causes the damage is not resolved, the inflammatory process progresses towards sub-acute/chronic inflammation, which is characterized by immunopathological changes, such as the infiltration of inflammatory cells, the overexpression of pre-inflammatory genes, the dysregulation of cellular signaling and the loss of barrier function. Chronic state of inflammation plays an important role in the onset of classic inflammatory diseases (e.g., arthritis) as well as other diseases, including cardiovascular and neurodegenerative diseases, diabetes, cancer, and asthma. The chronic pathological pain state, including neuropathic pain, is a leading health problem worldwide as it endures beyond the resolution of the pain source and can deeply impact quality of life. See Reference 4. The quality of life of neuropathic pain patients is furthermore often aggravated by comorbidities such as sleep disorders, depression and anxiety. Unlike physiological pain in which tissue injury and/or inflammation can reduce reversible adaptive changes in the sensory nervous system leading to protective sensitization, changes in sensitivity become persistent or chronic in neuropathic pain.

Furthermore, the nervous system, peripheral or central, is injured in neuropathic pain. It is characterized by pain in the absence of a noxious stimulus and may be spontaneous in its temporal characteristics or be evoked by sensory stimuli. There is no effective treatment with which to prevent or reverse neuropathic pain. See Reference 5. Therefore, treatment of chronic pain is still an unmet clinical need, as adequate pain relief is obtained by using drugs with adverse effects on the central nervous system side.

The finding of the endocannabinoid-mediated retrograde synaptic signaling pathway has opened up a new era for cannabinoid research and applications. Studies have shown that cannabinoid receptor agonists block pain in various acute and chronic pain models and that inflammation is attenuated. The CB2 receptor is thought to be particularly important in central neuronal pain circuits, as agonist activity induces dopamine release in mid-brain areas, contributing to descending pain control and the placebo effect. Inflammatory effects can either be modulated via the upregulation of cannabinoid receptor activity or increased production of endocannabinoids, providing an attenuation in joint destruction in rheumatoid arthritis models. Data from clinical trials on synthetic and plant-derived-based medicines have suggested that they are a promising approach for management of chronic neuropathic pain of different origins. See Reference 6. It is also hypothesized that reduces the alterations in cognitive and autonomic processing that are present in chronic pain states. See Reference 7. The frontal-limbic distribution of CB receptors in the brain suggests that may preferentially target the affective qualities of pain. Furthermore, may improve neuropathic pain reducing the low-grade inflammation consistent in the pathology. See Reference 8. Considering as a whole the problems of chronic neuropathic pain syndromes with a poorly understood pathogenesis, a complexity of symptoms and the lack of an optimal treatment, the potential of a therapeutic treatment strategy centered on cannabinoids is desirable.

Formulations of cannabinoids play a crucial role in creating solubility and physicochemical stability of cannabinoid drugs. Commonly used strategies in marketed products include salt formation (i.e., pH adjustment), co-solvency (e.g., ethanol, propylene glycol, PEG 400, etc.), micellization (e.g., polysorbate 80, cremophor ELP, etc.), nano-micro emulsification, complexation (e.g., cyclodextrins), and encapsulation in lipid-based formulations (e.g., liposomes) and nanoparticles. See References 10 and 12.

Various administration and delivery forms have been tested for therapeutic use. Cannabis products are commonly either inhaled by smoking/vaporization or taken orally. The pharmacokinetics and dynamics of cannabinoids vary as a function of the route of administration, with absorption showing the most variability of the principal pharmacokinetic steps. Absorption, in turn, is affected both by intrinsic product lipophilicity and by inherent organ tissue differences (i.e., alveolar, dermal, gastric). It is therefore an object of the present invention to provide a method of treatment in mammals (e.g., humans) for transdermal administration of one or more therapeutic agents or drugs wherein the therapeutic agent or drug is a cannabinoid.

Specifically, it is an object of the present invention to provide methods for treatment of: seizures; encephalopathy, including lethargy, focus/attention problems, and cognitive issues; weakness (e.g., muscle weakness); pain, including chronic pain, lower back pain, fibromyalgia, headaches and migraines; numbness; anxiety and other mood disorders; hypertension; insomnia; glaucoma; AIDS; cancer; PTSD; lack of appetite; arthritis; nausea and/or vomiting, as well as other conditions or disease states that may be treated with a cannabinoid. In preferred embodiments, the one or more therapeutic agent or drug comprises one or more cannabinoids useful for the treatment of such diseases or conditions that may be treated with such therapy (hereinafter referred to as "cannabinoid drug").

In preferred embodiments, the drug comprises one or more cannabinoids ("cannabinoid drug"). The cannabinoids may be derived from an endocannabinoid, a phytocannabinoid, a synthetic cannabinoid, or mixtures of any of the foregoing. In certain embodiments, the one or more cannabinoids comprises cannabidiol (CBD).

According to an aspect of the invention, a cannabinoid drug is preferably incorporated into a pharmaceutically acceptable composition suitable for topical application. Specifically, the pharmaceutical composition used in embodiments of the invention comprises one or more cannabinoids or chemical components thereof, wherein the one or more cannabinoid is selected from the group consisting of tetrahydrocannabinol (THC), cannabinol (CB), cannabidiol (CBD) and cannabichromene (CBC). The cannabinoid drug may be in the form of a base or may be provided as a pharmaceutically acceptable salt (inorganic or organic) or complex. It may be in an optically pure form or a mixture of stereoisomers. In preferred embodiments, the cannabinoid used in embodiments of the invention is not psychoactive, or only mildly psychoactive.

Cannabidiol (CBD) is not psychoactive; therefore, in certain preferred embodiments, the cannabinoid drug comprises CBD, or consists essentially of CBD, or consists of CBD. The CBD may be derived from crystalline powder, such that the powder is about 95% or more pure CBD. In embodiments of the invention, CBD makes up from about 5% to about 99% of the total amount of cannabinoids included in the pharmaceutically acceptable compositions used in methods of the invention. In particular, pharmaceutically acceptable compositions used in embodiments of the invention comprise at least 20% CBD (wt. %) based on a total amount (100 wt. %) of cannabinoids in the composition. For example, suitable pharmaceutical compositions may comprise CBD in an amount of about 30%, about 40%, about 50%, about 60%, about 70%, about 80%, about 90% or more, or greater than about 95% of the total amount of cannabinoids in the composition.

The "drug" administered according to embodiments of the invention may comprise CBD in combination with at least one other cannabinoid. In some embodiments, the cannabinoid drug comprises CBD in combination with THC (and optionally other cannabinoids). As CBD and THC have different mechanisms of action, they may act synergistically in what is known as the "entourage effect." In fact, many studies have now suggested that cannabinoid compounds work together to produce a synergistic effect (the "entourage effect"). Therefore, in certain embodiments, the formulations of the invention contain more than one cannabinoid compound. For example, the cannabinoid drug may be a cannabinoid such as: an endocannabinoid (generally derived from foods); a phytocannabinoid (derived from a plant or extracts), such as THC, CBD, CBN, etc.; and synthetic cannabinoids, such as THC; and mixtures thereof. In certain embodiments, a synthetic cannabinoid is used. Synthetic cannabinoids encompass a variety of distinct chemical classes: the classical cannabinoids structurally related to THC, including the nonclassical cannabinoids, arylsulfonamides, and eicosanoids related to the endocannabinoids.

Cannabigerol (CBG) is non-psychomimetic but still impacts the overall effects of cannabis. Specifically, CBG exhibits anti-inflammatory and analgesic properties, and evidence suggests that it may play a role in anti-viral effects, may have antidepressant effects, and may contribute to the overall analgesic effects of cannabis. In certain embodiments, the cannabinoid drug may alternatively or further comprise industrial hemp or a non-psychoactive hemp product.

In still further embodiments, the cannabinoid drug comprises a natural cannabinoid compound, a synthetic cannabinoid compound, a semi-synthetic cannabinoid compound, or mixtures thereof. Illustrative of such compounds are cannabinoids or cannabinoid analogues selected from the group consisting of cannabinol, cannabidiol, delta 9-tetrahydrocannabinol, delta 8-tetrahydrocannabinol, hydroxy-tetrahydrocannabinol, 11-hydroxy-9-tetrahydrocannabinol, levonantradol, delta-li-tretrahydrocannabinol, tetrahydrocannabivarin, dronabinol, amandamide, nabilone, a natural or synthetic analogue thereof, a natural or synthetic molecule with a basic cannabinoid structure, and mixtures of any of the foregoing.

Cannabis terpenoids (e.g., limonene, myrcene, a-pinene, linalool, nerolidol and phytol) share a precursor with phytocannabinoids that have been designated Generally Recognized as Safe by the U.S. Food and Drug Administration and other regulatory agencies. Terpenoids are generally quite potent and affect animals and humans when inhaled from ambient air. Thus, in certain embodiments, the formulations or compositions used in methods of the invention may include a therapeutic agent or drug (i.e., cannabinoid drug) that comprises both a phytocannabinoid and a terpenoid. In embodiments of the invention, such phytocannabinoid-terpenoid combinations and interactions may produce synergy with respect to treatment of pain, inflammation, depression, anxiety, addiction, epilepsy, cancer, and fungal and bacterial infections.

It is further within the scope of the invention to provide a pharmaceutical composition comprising a therapeutically effective amount, or an extract consisting essentially of a therapeutically effective amount, of at least one cannabinoid selected from the group consisting of CBD or a derivative thereof, THC or a derivative thereof, and any combinations thereof for use in treatment of the diseases and conditions discussed herein. In embodiments, the concentration of the CBD and/or THC and/or the derivatives thereof is preferably in a range of 2% to 80%, respectively. Specifically, pharmaceutically acceptable compositions used in embodiments of the invention may comprise CBD and THC (or derivatives thereof) in a ratio of from 0-1:1-0 of CBD:THC, including for example, more than 80% CBD and less than 20% THC.

An example of forming the preparation involves drying and grinding to a fine powder a plant material. This powder is then refluxed with alcohol or petroleum for 3 to 4 hours to separate the oils from the plant cellulose mass. The resulting extract is further purified and concentrated by removing tars and waxes with an alcohol petroleum ether and water wash. The remaining purified oil is separated from residual solvent through a distillation. The purified liquid is mixed with a carrier and any one or combination of permeation enhancer materials in selected concentrations to produce the preparation. An oil may first be added to the carrier to facilitate dissolution of the components. The resultant mixture may then be optionally heated. In embodiments, the pharmaceutical composition comprising at least one drug or derivative thereof further comprises at least one pharmaceutically acceptable excipient (inactive ingredient) selected from the group consisting of: antiadherent, binder, disintegrant, lubricant, preservative, filler, emulsifier, humectant, thickener, skin nourishing agent, emollient agent, calming agent, natural smell agent, suspending agent, pH adjustment agent, and any combinations thereof. For example, the pharmaceutical composition may comprise at least one pharmaceutically acceptable excipient selected from the group consisting of purified water, Glyceryl Stearate, PEG-100 Stearate, Glycerin, Cetyl Alcohol, Shea Butter, Petrolatum, Steareth-21, Lavender Oil, Xanthan Gum, Aloe Leaf Juice, Triethanolamine, Bisabolol, Allantoin, Disodium EDTA and any combination thereof.

Liquid or gel carriers may include carbon tetrachloride, ethanolic solutions of resin and pyrahexyl mixed with THC, Tween 80 or petrol ether. Other suitable carriers include natural rubber blends, viscoelastic semi-solids (such as pressure sensitive adhesive materials), hydrogels, soft thermoplastic polymers (such as ethylene vinyl acetate with high VA contents), elastomers (such as polyisoprene elastomers) and thermoplastic elastomers (such as styrene-butadiene block copolymers. As a further example, the carrier may be an aqueous-based cannabidiol cream produced using LIPODERM as the carrier. LIPODERM/LIP is a whitish cream with no smell, commercially marketed compounding agent (from PCCA, Pharmaceutical Compounding Centers of America) having the following ingredients: Ethoxydiglycol, Water (Aqua), Glycerin, $C_{12-15}$ Alkyl Benzoate, Glyceryl Stearate, Dimethicone, Cetearyl Alcohol, Cetearyl Glucoside, Polyacrylamide, Cetyl Alcohol, Magnesium Aluminum Silicate, Xanthan Gum, Aloe Vera (Aloe Barbadensis), Tocopheryl Acetate (Vitamin E Acetate), *Prumus amyadalus amara* (Bitter Almond) Kernel Oil, *Vitis vinifera* (Grape) Seed Extract, *Triticum vulgare* (Wheat) Germ Oil, Retinyl Palmitate (Vitamin A Palmitate), Ascorbyl Palmitate (Vitamin C Palmitate), Pro-Lipo Multi-emulsion Liposomic System, Tetrasodium EDTA, Phenoxyethanol, and Sodium Hydroxymethylglycinate.

Additional carriers are also intended to be within the scope of the invention, and persons skilled in the art will recognize that topical carriers meeting specific chemical requirements of an individual drug can be formulated for maximum efficiency in topical delivery. However, the carrier material should be inert to the cannabis drug and permit easy migration of the topical pharmaceutically acceptable composition to a patient's skin.

In embodiments, compositions of the invention comprising the therapeutic agent to be administered preferably include a topically acceptable carrier or adjuvant for improved dispensing and application of such compositions. The compositions may be in the form of a paste, gel, cream, lotion, solution, or emulsion. Pastes are liquids with enhanced viscosity whereby flow is inhibited by the presence of undissolved and dissolved solids (e.g., waxes, inorganic solids, etc.). Gels are semisolid systems either containing suspended small inorganic particles (two phase gels) or organic macromolecules interpenetrated by a liquid (single phase gels). Emulsions, lotions, and creams are multiphase liquids containing surfactants that inhibit or delay the separation of the phases.

In certain embodiments, pharmaceutical compositions according to embodiments of the invention may further comprise one or more of pharmaceutical grade light mineral oils, vegetable oils, fish and animal oils, and *cannabis* oils. In certain embodiments, the pharmaceutical composition may comprise about 5% to about 70% *cannabis* oil, such as, e.g., from about 10% to 30% *cannabis* oil. For example, the pharmaceutical composition may comprise about 10% of a *cannabis* oil comprising about 20% THC and about 40% CBD, wherein the final formulation of the pharmaceutical composition comprises 2% THC and 4% CBD. In certain embodiments, pharmaceutically acceptable compositions for use in embodiments of the invention comprise a cannabinoid drug, an oil, and a liquid or gel carrier. The amount of carrier can range from about 10-90 wt. % of the overall composition and the oil may be present in a range of 1-90 wt. % of the overall composition.

Suitable carriers and adjuvants according to embodiments of the invention are selected based on being safe in prolonged or even indefinite applications of the subject composition. In embodiments, carriers and adjuvants suitable for use include: solvents, such as ethanol, ethyl acetate, glycerine, polyethylene glycols with average molecular weights ranging from 200-1100, and propylene glycol (water miscible), heptane, purified isoparaffinic hydrocarbons boiling in the range of 60-300° C. and fractions thereof, canola oil, olive oil, and mineral oil (not miscible with water); emollients, such as petrolatum, paraffin wax, beeswax, cetyl palmitate, and lanolin; emulsifiers and surfactants, such as sodium, potassium, and triethanolamine salts of oleic and stearic acids, dioctyl sodium sulfosuccinate, sodium dodecyl sulfate, glycerol monooleate, glycerol monostearate, and ethoxylated sorbitan esters such as Polysorbate 20, Polysorbate 65 and Polysorbate 80; finely divided solids such as aluminum hydroxide, bentonite, kaolin, magnesium silicate, silica, titanium dioxide, and zinc oxide; thickeners, such as agar, carrageenan, food starch, modified starch, gelatin, gum arabic, guar gum, hydroxyethylcellulose, hydroxypropyl methylcellulose, pectin, sodium carboxymethylcellulose and polyacrylic acid adjusted in pH to provide the desired extent of thickening; and antioxidants and preservatives, such as benzoalkonium chloride, di-coo-dimethylammonium chloride, dilauryl thiodipropionate, methyl parahydroxybenzoate, propyl parahydroxybenzoate, and tocopherol.

Preferred carries and adjuvants include medium chain length triglycerides having 6-10 carbon atoms in each fatty acid chain, straight chain aliphatic alcohols having 12-20 carbon atoms, ethanol, and water. In embodiments where the composition is a solution, the composition may include volatile carriers such as ethanol and water, as well as non-volatile carriers such as medium chain length triglyceride and straight chain aliphatic alcohols having 12-20 carbon atoms to supplement or substitute for volatile carriers.

As it has been determined that skin permeability of *cannabis* is relatively low, an increase in permeability may be accomplished through use of permeation enhancers. The enhancer that results in the highest skin flux is often specific to a particular drug, and what works for one drug may not work for another. Furthermore, the precise concentration of enhancer and the particular combination of enhancers must be tailored to each drug to achieve the maximum skin flux. There are numerous permeation enhancers suitable for use in embodiments of the invention and they are typically categorized into two groups: solvent-type enhancers and plasticizing-type enhancers.

Plasticizer-type enhancers refer to fatty acids, fatty acid esters, fatty alcohols and similar hydrophobic compounds that are capable of increasing the permeability of drugs to the stratum corneum. Without limiting the scope of the present invention, the following is proposed as the mechanism of action of the plasticizer-type enhancers. It is believed that the function of the plasticizer-type enhancers is to migrate into the upper stratum corneum layers of the skin and disrupt the lipids which occupy the extracellular spaces of the stratum corneum. The stratum corneum layer, although only 25-50 microns thick, is the principal barrier to transdermal permeation. The plasticizer-type enhancers that migrate into the skin serve to increase the mobility and diffusion of the drug into the skin. Typically, plasticizer-type enhancers have a molecular weight between 150 and 1000, and should be relatively water insoluble so as to not leach into the subcutaneous tissue layers below the stratum corneum. In preferred embodiments, plasticizer-type enhancers with a water solubility of less than 0.5 wt % or even 0.2 wt % or less are used.

Solvent-type enhancers, on the other hand, generally refer to relatively hydrophilic compounds having molecular weights of less than about 200 that are capable of increasing the permeability of drugs to the stratum corneum. Solvent-type enhancers typically exhibit solubility parameters between about 10 and 24, and preferably between about 10 and 18. Typically, solvent type enhancers comprise a pharmaceutically-acceptable lower alkyl alcohol aryl alcohol, or polyol, for example, ethanol, propanol, butanol, benzyl alcohol, glycerin, or propylene glycol. In some embodiments, the solvent-type enhancer is a 2-pyrrolidone or alkyl derivative thereof, such as N-methyl-2-pyrrolidone, 3-hydroxy-N-methyl-2-pyrrolidone, and pyroglutamic acid esters. In embodiments, preferred solvent type enhancers have a molecular weight of less than about 150, are relatively hydrophilic, generally being at least 2 wt % soluble in water, and preferable at least 10 wt % soluble in water. In some embodiments, solvent type enhancers may be used that are completely water miscible.

While solvent type enhancers may be useful in delivering larger amounts of therapeutic agent through the skin, when used alone, larger amounts of the solvent enhancer must typically be continuously applied to achieve a prolonged therapeutic effect because the enhancers are themselves permeable through the skin. Therefore, using one or more plasticizer-type enhancers in combination with one or more solvent-type enhancers may be desirable to achieve drug delivery through the stratum corneum at therapeutically effective levels. When used in combination with plasticizer-type enhancers, the function of the solvent type enhancer is to rapidly diffuse into the stratum corneum layer of the skin, making it possible for the larger, less mobile plasticizer-type enhances to enter the stratum corneum layer.

In certain embodiments of the invention, the pharmaceutically acceptable composition comprises a permeation enhancer in an amount of about 1-50 wt. % of the overall composition comprising the *cannabis* drug (and/or one or more other drug). The most effective enhancers are nonionic surfactants or solvents having an HLB value from about 6 to 30. The term "HLB" is a numeric expression of the ability to emulsify non-soluble ingredients in oil and water.

Permeation enhancers may be selected from chemical groups of glycerol esters, polyglycerol esters, alkyl fatty acid esters, ethoxylated sorbitan esters, alcohol ethoxylates, lanolin ethoxylates, ethoxylated fatty methyl esters and alkanol amides. Examples of effective permeation enhancer materials having an HLB from 8-10 include: PEG 200 monolaurate, sorbitan monolaurate, POE myristyl ether, POE lauryl alcohol, POE sorbitan monooleate, octyphenoxypoly ethanol, linear alcohol ethoxylate, mono and diglycerides with polysorbate 80, nonyl phenol ethoxylate, alkylaryl polyester ethanol, and N,N-dimethyl amide. Examples of effective permeation enhancer materials having an HLB from 11-14 include: PEG 400 monooleate, polyoxyaryl ether, PEG 600 monooleate, POE sorbitan monooleate, PEG 400 monolaurate, POG lauryl alcohol, and nonylphenoxypolyethanol. Examples of permeation enhancer materials having n HLB form 15-28 include: nonyl phenol ethoxylate, castor oil ethoxylate, ethoxylated cocomonoglyceride, oleylalcohol condensed ethylene oxide, modified oxyethylated straight chain alcohol, ethoxylated lanolin alcohol, nonylphenyl ethoxylate, polyethylene 100 stearyl ether, ethoxylated polyoxypropylene glycols, and ethoxylated polyoxypropylene glycols.

In preferred embodiments, penetration enhancers useful in the formulations of the present invention include, but are not limited to, isostearic acid, octanoic acid, oleic acid, oleyl alcohol, lauryl alcohol, ethyl oleate, isopropyl myristate, butyl stearate, methyl laurate, diisopropyl adipate, glyceryl monolaurate, tetrahydrofurfuryl alcohol polyethylene glycol ether, polyethylene glycol, propylene glycol, 2-(2-ethoxyethoxy)ethanol, diethylene glycol monomethyl ether, diethylene glycol monoethyl ether, alkylaryl ethers of polyethylene oxide, polyethylene oxide monomethyl ethers, polyethylene oxide dimethyl ethers, dimethyl sulfoxide, glycerol, ethyl acetate, acetoacetic ester, N-alkylpyrrolidone, and terpenes.

Suitable permeation enhancer compositions that may be included in the formulations or pharmaceutical compositions include (but are not limited to) dimethylsulfoxide (DMSO), N,N-dimethylacetamide (DMA), decylmethylsulfoxide ($C_{10}$MSO), polyethylene glycol monolaurate (PEGML), propylene glycol (PG), PGML, glycerol monolaurate (GML), lecithin, the 1-substituted azacycloheptan-2-ones, particularly 1-n-dodecylcyclazacycloheptan-2-one (available under the trademark AZONE from Whitby Research Incorporated, Richmond, Va.), alcohols, and the like. The permeation enhancer may also be a vegetable oil as described in U.S. Pat. No. 5,229,130 to Sharma. Such oils include, for example, safflower oil, cotton seed oil and corn oil. Additional optional enhancers for use in embodiments of the present invention are lipophilic compounds having the formula $[RCOO]_nR'$, wherein $_n$ is 1 or 2, R is a $C_1$-$C_{16}$ alkyl optionally substituted with 1 or 2 hydroxyl groups, and R' is hydrogen or $C_1$-$C_{16}$ alkyl optionally substituted with 1 or 2 hydroxyl groups. Within this group, a first subset of compounds are represented by the formula $[CH_3(CH_2)_mCOO]_nR'$ in which m is an integer in the range of S to 16, $_n$ is 1 or 2, and R' is a lower alkyl ($C_1$-$C_3$) residue that is either unsubstituted or substituted with one or two hydroxyl groups Preferred enhancers within this group include an ester which is a lower alkyl ($C_1$-$C_3$) laurate (i.e., $_m$ is 10 and $_n$ is 1) such as "PGML." It will be appreciated by those skilled in the art that the commercially available material sold as "PGML" is typically, although not necessarily, a mixture of propylene glycol monolaurate itself, propylene glycol dilaurate, and either propylene glycol, methyl laurate, or both. Thus, the terms "PGML" or "propylene glycol monolaurate" as used herein are intended to encompass both the pure compound as well as the mixture that is typically obtained commercially. Also within this group is a second subset of compounds, namely, esters of fatty alcohols represented by the formula $CH_3(CH_2)_m$—O—CO—$CHR_1R_2$, in which $R_1$ and $R_2$ are independently hydrogen, hydroxyl, or a lower alkyl ($C_1$-$C_3$), and m is as above. Particularly preferred enhancers within this group are lauryl lactate and myristyl lactate. In addition, a third subset of compounds within this group are analogous fatty acids. i.e, acids having the structural formula $CH_3(CH_2)_mCOOH$, where m is as above. A particularly preferred acid is lauric acid.

Other optional enhancer compositions include those where a lipophilic compound as just described, particularly PGML, is combined with a hydrophilic compound, such as a $C_2$-$C_6$ alkanediol. One particular hydrophilic enhancer within this group is 1,3-butanediol. Such enhancer compositions are described in detail in PCT Publication No. WO 95/05137, published Feb. 23, 1995, herein incorporated by reference. Another hydrophilic enhancer that may be included in these compositions is an ether selected from the group consisting of diethylene glycol monoethyl ether (Transcutol) and diethylene glycol monomethyl ether. Such enhancer compositions are described in detail in U.S. Pat. Nos. 5,053,227 and 5,059,426 to Chiang et al., the disclosures of which are herein incorporated by reference. Other optional enhancer compositions may include one or more mixtures or combinations of any of the aforementioned enhancers, and the like.

The topical formulations or pharmaceutical compositions of the present invention (e.g., ointments, gels, creams, or the like), must be suitable for topical administration of the at least one *cannabis* drug and any optional additional drug(s) i.e., must contain pharmaceutically acceptable excipients compatible with application to the skin tissue, and may optionally contain a sufficient amount of an enhancer composition as described hereinafter.

As but one example, a pharmaceutical composition suitable for use in embodiments of the invention comprises least one *cannabis* drug, preferably in oil, together with a suitable amount of a penetration enhancer, dimethyl sulfoxide, and a base. For example, such a composition may include CBD oil, and about 3 ml dimethyl sulfoxide in 30 g of base. The CBD can be incorporated at a concentration of, e.g., from about 0.5% to about 25% of the topical composition, such as from about 1% to about 20%, or from 1% to 10% In certain preferred embodiments, the CBD is present in a concentration ranging from 1% to 5%. The dosage of a composition comprising a CBD concentration of 1.5% to 3% (as an example) equates to a composition dose of from about 0.5 g to about 1 g when applied topically on a skin surface of a subject.

U.S. Patent Application Publication No. 2008/0112895, incorporated by reference herein, describes a room temperature stable aqueous cannabinoid formulation comprising an effective amount of a cannabinoid in a semi-aqueous solution buffered to a pH of about 5-1, the solution comprising water and an effective amount of an organic cosolvent to maintain the physical stability of the formulation, which may be incorporated into a pharmaceutically acceptable carrier. Therefore, in certain embodiments the topical formulation may include at least one water-insoluble, pharmacologically approved, alkyl cellulose or hydroxyalkyl cellulose, and the like. Alkyl cellulose or hydroxyalkyl cellulose polymers for use in compositions in embodiments of the invention include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or across linking agent may be used to modify the polymer's characteristics. For example, esters such as dibutyl or diethyl phthalate, amides such as diethyldiphenyl urea, vegetable oils, fatty acids and alcohols such as acid oleic and myristyl may be used in combination with the cellulose derivative.

The topical pharmaceutical compositions may further include hydrocarbons such as liquid paraffin, qualene, solid paraffin, microcrystalline wax, etc.; higher aliphatic alcohols such as cetyl alcohol, hexadecyl, alcohol, stearyl alcohol, oleyl alcohol, etc.; esters of higher fatty acids with higher alcohols such as beeswax, etc.; esters of higher fatty acids with lower alcohols such as isopropyl myristate, isopropyl palmitate, etc.; vegetable oils, modified vegetable oils, hydrous lanolin and its derivative, squalene, 43qualene; higher fatty acids such as palmitic acid, stearic acid, etc., and the like.

In certain embodiments, the pharmaceutical compositions may further include emulsifiers and dispersing agents which include, for example, anionic, cationic and nonionic surfactants. Nonionic surfactants are preferred because of their low levels of irritation to skin Typical of nonionic surfactants are fatty acid monoglycerides such as glyceryl monostearate, etc.; sorbitan fatty acid esters such as sorbitan monolaurate, etc.; sucrose fatty acid esters; polyoxyethylene fatty acid esters such as polyoxyethylene stearate, etc.; and polyoxyethylene higher alcohol ethers such as polyoxyethylene cetyl ether, polyoxyethylene oleyl ether, etc.

In certain preferred embodiments, the topical TRNA formulation is aqueous-based. In certain embodiments, the topical composition may include a gelling agent such as methylcellulose, ethylcellulose, hydroxyethylcellulose, hydroxypropyl-cellulose, hydroxypropylmethylcellulose, carboxymethylcellulose, carbomer, and the like. Examples of pharmaceutical compositions which rely upon an aqueous gel composition as a vehicle for the application of a drug are provided in U.S. Pat. Nos. 4,883,660; 4,767,619; 4,511,563; 4,861,760; and 5,318,780, the disclosures of which are herein incorporated by reference.

In certain embodiments, a topical pharmaceutical composition comprises: at least one drug in an amount of from 0.1 to 80% by weight, preferably 1 wt. % to 50 wt. %; and from 5 wt. % to about 30.0 wt. %, preferably from about 1 wt. % to about 30 wt. % of a permeation enhancer composition, with the remainder of the composition comprising a carrier or vehicle. In preferred embodiments, the at least one drug comprises one or more *cannabis* drug, and optionally may comprise additional drug(s) suitable for treating or alleviating symptoms of a disease or condition of the subject. In certain preferred embodiments, the at least one drug is included in a cream or gel or ointment in a concentration of, e.g., 1 mg drug/ml of carrier (e.g., Lipoderm). However, it is to be understood that a person skilled in the art could increase the amount of carrier or change the specific carrier to maintain or improve efficacy of the topical composition in the treatment methods of the invention in preferred embodiments, the at least one drug comprises at least one *cannabis* drug, and optionally one or more additional drug(s) therapeutically effective for treating or alleviating acute pain or chronic pain associated with a disease or condition of a subject.

The topical formulations of the present invention (e.g., ointment, gel, cream, or the like), must be suitable for topical administration of the at least one *cannabis* drug and any optional additional drug(s), i.e., must contain pharmaceutically acceptable excipients compatible with application to the skin tissue, and may optionally contain a sufficient amount of an enhancer. In certain embodiments, topical pharmaceutical compositions suitable for use in embodiments of the invention comprise: at least one drug formulated in an ointment, gel, cream or the like, in an amount of from 0.1 to 80% by weight, preferably 1 wt. % to 50 wt. %; and from 5 wt. % to about 50.0 wt. %, preferably from about 1 wt % to about 30 wt % of a permeation enhancer composition, with any remainder of the composition comprising a carrier or vehicle. The at least one drug is preferably included in a cream or gel or ointment in a concentration of, e.g., 1 mg drug/ml of carrier (e.g., Lipoderm). However, it is to be understood that a person skilled in the art could increase the amount of the carrier or vehicle, or change the specific carrier to maintain or improve efficacy of the topical composition in the treatment methods of the invention. In preferred embodiments, the at least one drug comprises at least one *cannabis* drug, and optionally one or more additional drug(s) therapeutically effective for treating or alleviating acute pain or chronic pain associated with a disease or condition of a subject.

In certain embodiments, the overall pharmaceutically acceptable composition preferably comprises 10-90 wt. % carrier, 5-60 wt. % therapeutic agent, 1-90 wt. % oil, and 1-15 wt. % permeation enhancer. In embodiments, the therapeutic agent is a *cannabis* drug.

In certain embodiments of the invention, the at least one cannabinoid drug is administered together with (e.g., in the same formulation), simultaneously (but separately), or sequentially with at least one additional active agent or drug suitable for treating a patient's disease state or condition. Depending on a subject's particular disease state or condition, classes of drugs suitable for use as the at least one additional drug to be administered with the cannabinoid drug include (without limitation) the drugs listed below.

In certain embodiments, the at least one additional drug includes a dopamine agonist such as apomorphine (APOKYN), pramipexole (MIRAPEXIN), ropinirole (REQUIP), bromocriptine (PARLODEL), cabergoline (CABACER, DOSTINEX), pergolide (PERMAX, CELANCE), rotigotine (NEUPRO), mixtures of any of the foregoing, or other dopamine agonists known to those skilled in the art. One skilled in the art will appreciate that dopamine agonists other than apomorphine may be used in the formulations and methods of the present invention, and all such agents are meant to be encompassed by the term "dopamine agonists." For example, such drugs include, but are not limited to, carbidopa (SINEMET), dopamine agonists (REQUIP, ROTIGOMIRAPEX), COMT inhibitors (ENTACAPONE, TOCAPONE), rasagiline (AZILECT), MAO inhibitors and MAO-B inhibitors, such as Selegiline (ELDEPRYL).

In certain embodiments, the at least one additional drug includes an opioid such as morphine, codeine, dihydrocodeine, hydrocodone, hydromorphone, nicomorphine, oxycodone, oxymorphone, fentanyl, alphamethylfentanyl, alfentanil, sufentanil, remifentanil, carfentanyl, ohmefentanyl, thebaine, oripavine, diacetylmorphine (heroin), phenylpiperidines such as pethidine (meperidine) and ketobemidone, allylprodine, prodine, propoxyphene, dextropropoxyphene, dextromoramide, bezitramide, piritramide, methadone, dipipanone, levomethadyl Acetate (LAAM), loperamide, diphenoxylate, dezocine, pentazocine, phenazocine, buprenorphine, dihydroetorphine, etorphine, butorphanol, nalbuphine, levorphanol, levomethorphan, lefetamine, meptazinol, tilidine, tramadol, tarpentadol, mixtures thereof, and the like.

In yet other embodiments, the at least one additional drug is tarpentadol (a centrally acting oral analgesic having two mechanisms of action combining mu-opioid receptor agonist and norepinephrine reuptake inhibitor).

In some embodiments, the at least one additional drug is a selective norepinephrine reuptake inhibitor, such as Atomoxetine (STRATTERA), Mazindol (MAZANOR, SANOREX), Nisoxetine (LY-94939), Reboxetine (EDRONAX, VESTRA), Viloxazine (VIVALAN), and mixtures thereof.

In yet other embodiments, the at least one additional drug is a benzodiazepine, such as lorazepam (ATIVAN), diazepam (VALIUM), clonazepam (KLONOPIN), chlordiazepoxide (LIBRIUM), alprazolam (XANAX), temazepam (RESTORIL), mixtures thereof, and the like. In other embodiments, the drug is a neuroleptic or psychotropic such as chlorpromazine (THORAZINE), haloperidol (HALDOL), risperidone (RISPERDAL), olanzapine (ZYPREXA), and quetiapine (SEROQUE).

In other embodiments, the at least one additional drug is an agent that treats depression and/or anxiety, for example, selective serotonin reuptake inhibitors (SSRIs) such as fluoxetine (PROZAC), sertraline (ZOLOFT), venlafaxine (EFFEXOR), citalopram (CELEXA), parocetine (Paxil), mixtures thereof, and the like (such as trazodone (Desyrel)), and/or serotonin-norepinephrine reuptake inhibitors (SNRI), (such as Desvenlafaxine (PRISTIQ), Duloxetine (CYMBALTA), Milnacipran (IXEL, SAVELLA), Venlafaxine (EFFEXOR)), mixtures thereof, and the like.

In yet other embodiments, the at least one additional drug is a norepinephrine-dopamine reuptake inhibitor (NDRI), such as Amineptine (SURVECTOR), an aminoketone antidepressant such as Bupropion (WELLBUTRIN, ZYBAN), Dexmethylphenidate (FOCALIN), Methylphenidate (RITALIN, CONCERTA), Nomifensine (MERITAL), a phenylpiperazine antidepressant such as nefazodone (SERZONE), a piperazino-azepine antidepressant such as mirtazapine (REMERON), mixtures thereof, and the like.

In yet other embodiments, the at least one additional drug may be an NMDA receptor antagonist. Although phencyclidine, ketamine, and dextromethorphan have been known to be used as recreational drugs, at subanesthetic doses these drugs have mild stimulant effects, and have shown promise for the treatment of conditions that involve excitotoxicity, including traumatic brain injury, stroke, and neurodegenerative diseases such as Alzheimer's, Parkinson's, and Huntington's.

Additionally, the at least one additional drug may be an agent that treats neuropathic/neurogenic pain (pain that arises from nerve dysfunction and not as a result of injury, (e.g., trigeminal neuralgia), such as carbamazepine, gabapentin, topiramate, zonisamide, phenytoin, desipramine, amitriptyline, imipramine, doxepin, protriptyline, pentoxifylline, and hydroxyzine.

In other embodiments, the at least one additional drug treats insomnia, such as zolpidem (AMBIEN). In other embodiments, the at least one additional drug treats fatigue. Such drugs include central nervous system stimulants such as pemoline (CYLERT) and Modafinil (PROVIGIL). In yet other embodiments, the at least one additional drug treats vertigo, nausea and/or dizziness, such as meclizine (ANTIVERT), dimenhydrinate (35qualene35), prochlorperazine (35QUALENE35), scopolamine (TRANSDERM) and diphenhydramine (BENADRYL).

In certain embodiments, the at least one additional drug is a serotonin-norepinephrine reuptake inhibitor (SNRI), such as Desvenlafaxine (PRISTIQ), Duloxetine (CYMBALTA), Milnacipran (IXEL, SAVELLA) Venlafaxine (EFFEXOR), mixtures thereof, and the like. In other embodiments, the at least one additional drug is a tricyclic antidepressant (TCA), such as Amitriptyline (ELAVIL), Butriptyline (EVAIDENE, EVADYNE), Clomipramine (ANAFRANIL) Desipramine (NORPRAMIN, PERTOFRANE), Dosulepin (PROTHIADE), Doxepin (ADAPIN, SINEQUAN), Imipramine (TOFRANIL) Lofepramine (FEPRAPAX, GAMANIL, LOMONT), Nortriptyline (AVENTYL, NORTRILEN, PAMELOR), Protriptyline (VIVACTIL) Trimipramine (SURMONTIL), mixtures thereof, and the like.

In yet other embodiments, the at least one additional drug is a tetracyclic antidepressant, such as Amoxapine (ASENDIN), Maprotiline (LUDIOMIL), Mianserin (MIANSERIN), mixtures thereof, and the like.

In some embodiments, the at least one additional drug is an atypical antipsychotic, such as Ziprasidone (GEODON, ZELDOX), Nefazodone (SERZONE), and the like.

In other embodiments, the at least one additional drug is an anti-convulsant or anti-epileptic drug such as arylsulfonimide analogues such as Acetazolimide (DIAMOX), tricyclic iminostilbene derivatives such as carbamazepine (TEGRETO), benzodiazepines such as clonazepam (KLONOPIN) clorazepate dipotassium (TRANXENE), lorazepam (ATIVAN) and diazepam (VALIUM), carboxylic acid derivatives such as valproic acid (DEPAKENE) and divalproex sodium (DEPAKOTE), succinimide derivatives such as ethosuximide (ZARONTIN), carbamate esters of 2-phenyl-1,3-propanediol such as felbamate (FELBATOL), hydantoins such as phenytoin (DILANTIN), phenytoin sodium (DILANTIN) and fosphenytoin sodium (CEREBYX), structural analogues of GABA such as gabapentin (NEURONTIN) and pregabalin (LYRICA), phenyltriazines such as lamotrigine (LAMICTAL), pyrrolidine derivatives such as levitiracetam (KEPPRA), tricyclic iminostilbene derivatives such as 36qualene36pine (TRILEPTAL), barbiturates such as Phenobarbital, desoxybarbiturates such as primidone (MYSOLINE), nipecotic acid derivatives such as tiagabine hydrochloride (GABITRIL), sulfamated monosaccharides such as topiramate (TOPAMAX), oxazolidinedione derivatives such as trimethadione (TRIDIONE), and methanesulfonamides such as zonisamide (ZONIGRAN).

In yet other embodiments, the at least one additional drug is an analgesic/anti-inflammatory agent such as acetaminophen; prednisone, solumedrol, and other steroids; and naproxen, aspirin, voltaren, ketoprofen, ibuprofen, nabumetone, and other NSAID's. The NSAID may be COX-1, COX-2 or mixed COX-1/COX-2 inhibitors. Examples of COX-2 inhibitors include oxicam, meloxicam, and the more selective celecoxib, rofecoxib, valdecoxib, parecoxib and etoricoxib. Further examples of corticosteroids include methylprednisolone, prednisolone, dexamethasone, and adreno-corticotrophic hormone (ACTH), corticotropin.

Additionally, the at least one additional drug may be an agent that treats neuropathic/neurogenic pain (pain that arises from nerve dysfunction and not as a result of injury, e.g., trigeminal neuralgia), such as carbamazepine, gabapentin, topiramate, zonisamide, phenytoin, desipramine, amitriptyline, imipramine, doxepin, protriptyline, pentoxifylline, and hydroxyzine, mixtures thereof, and the like. In other embodiments, the at least one additional drug is 4-aminopyridine (4-AP; also known as FAMPRIDINE) or a pharmaceutically acceptable derivative thereof. This drug has been shown to have the ability to improve the communication between damaged nerves, which may result in increased neurological function in the treatment of conditions such as multiple sclerosis (MS). An example of another such drug is 3,4 diaminopyridine.

In other embodiments, the at least one additional drug is useful for the treatment of Dementia/Alzheimer's disease, such as ARICEPT/donepezil, EXELON/rivastigmine. REMINYL/RAZADYNE/galantamine, and NAMENDA/memantine, their naturally occurring counterparts, and mixtures thereof.

All currently approved therapies for the conditions described above reach the central nervous system through systemic circulation, and cerebral blood flow to brainstem structures is through posterior circulation, via the vertebral and basilar arteries and their branches. An object of the present invention is to provide a method for topical administration and improved transdermal delivery of currently used drugs, in combination with a cannabinoid drug, and optionally compounded with a suitable dermal penetration enhancer in a liquid, gel, or cream form, optionally in a sustained-release formulation, to a skin surface via the transdermal patch and treatment methods of the invention described in more detail below. An example of a commercially available compounding medium suitable for use in the present invention is LIPODERM. In addition, persons skilled in the art will recognize that various other topical carriers meeting the specific chemical requirements of an individual drug can be formulated for maximum efficiency in topical delivery.

Depending on a subject's condition or associated symptoms being treated, the formulations and pharmaceutical compositions are prepared such that the at least one *cannabis* drug, and any optional additional drug(s), can be delivered acutely in single dose applications as a cream/gel/ointment/liquid, and optionally in a sustained or controlled release form, via a transdermal patch as described herein. By virtue of the methods of the invention, the disease state or condition and/or associated symptoms to be treated are treated much faster and more effectively than prior art modes of administration of the referenced drug(s). Alternatively, the at least one *cannabis* drug, and any optional additional drug(s), can be topically applied to a preferred portion of the subject's skin as a unit dose in a cream, ointment, gel or liquid in immediate release form, via the transdermal patch described herein. In such instances, the concentration of *cannabis* drug(s) included in the unit dose preferably range from 1 mg to about 100 mg, based on CBD, or a therapeutically equivalent amount of another cannabinoid drug(s) In certain embodiments, a unit dose of cannabinoid (e.g., CBD) may range from about 10 mg to about 60 mg or from about 20 mg to about 40 mg. This may be administered in a topical cream, ointment, gel or the like. For example, the topical composition may be administered as a unit dose in an amount ranging from about 0.5 g to about 1 g at a cannabinoid (e.g., CBD) concentration from about 0.1% to about 5% (or more).

III. Ultrasound System and Transdermal Patch

The skin is a multi-layered organ. The stratum corneum, which is the outermost layer of the skin, presents the principal resistance to the penetration of topically applied compounds, such that the number of molecules currently used in topical and cosmetic dermal delivery is quite limited. It is therefore an object of the present invention to more effectively deliver drugs, such as in the form of a pharmaceutical composition, to the stratum corneum for transdermal absorption.

In furtherance of the above objective, ultrasonic waves have been used in medical applications, including diagnostics and therapy. Diagnostic use of ultrasound waves includes using ultrasonic waves to detect underlying structures in an object or human body by placing an ultrasonic transducer in contact with the tissue or object via a coupling medium and directing high frequency (1-10 MHz) ultrasonic waves to the tissue. Upon contact with the various underlying structures, the waves are reflected back to a receiver adjacent to the transducer, and an image of the underlying structure can be produced by comparing the signals of the ultrasonic waves sent with the reflected ultrasonic wave that is received. Therapeutic medical uses of ultrasound waves include aerosol mist production, contact physiotherapy, and soft tissue ablation. Beneficial effects have been reported from contact ultrasound physiotherapy, including local improvement of blood circulation, heating of the tissue, accelerated enzyme activity, muscle relaxation, pain reduction, and enhancement of natural healing processes.

Despite the above beneficial effects, current techniques of medical physiotherapy using ultrasonic waves are limited by the need for a direct contact interface between the ultrasonic transducer and the tissue in order to maintain an effective transmission of the ultrasonic waves from the transducer to the tissue. As such, conventional contact ultrasound may have a destructive effect on, for example, open wounds due to the close proximity of an oscillating tip of an ultrasonic transducer relative to the potentially damaged tissue surface. The necessity of direct contact with or without a coupling medium makes conventional ultrasound treatments unsuitable for many applications, including, for example, treatment of fresh or open wounds.

Furthermore, conventional ultrasound used for therapy may be of high frequency (1-4 MHz) and/or low frequency (20-120 KHz), and may have longitudinal or transverse characteristics. Embodiments of the present invention include excitement of surface acoustic waves on the skin (low power, low frequency) and employing this phenomenon for therapeutic purposes. Based on research conducted by the inventors of the portable SAW-generating device, it was found that low-power, low-frequency ultrasound (20-120 KHz, 0.05-1.0 W/cm$^2$) propagated in the form of surface acoustic waves is effective for one or more of the following: inhibiting adhesion, micro-massage, healing processes, tissue fluid interchange, increased capillary growth, increased pH of tissue liquids, lowered pain, resistance of thrombus formation, improved drug administration, reduced friction, cleansing of tissues, removal of necrotic debris, disinfection, “biostimulation” of cells, improved blood flow, drying, intensity of drug diffusion, and increased activity of coating agents.

According to the present invention, provided is a transdermal patch that is an ultrasound conductive patch configured for use in tandem with the portable ultrasound generating system described herein so as to also transmit ultrasound energy (SAW) into tissues for enhanced topical absorption the therapeutic agent. Specifically, a transdermal patch as described herein is configured to comprise a therapeutically effective amount of a therapeutic agent, such as a drug, preferably comprising a *cannabis* drug, and to provide for enhanced and controlled delivery of the therapeutic agent to the subject through application of SAW.

A transdermal patch according to embodiments of the invention is provided as the application means for delivery of a therapeutically effective amount of a drug and surface acoustic waves (SAW) for improved or optimized absorption. Specifically, the transdermal patch is configured to efficiently couple ultrasound energy into tissues for significantly improved delivery and absorption of the at least one therapeutic agent (e.g., a pharmaceutical composition comprising a *cannabis* drug) comprised therein.

In embodiments, the transdermal patches may have a variety of shapes, but rounded shapes are preferred as they contain no corners, thus making them less easily detached from the skin. The transdermal patches may be a disposable one-time use patch or a more extended use patch for periods of use ranging from 24 hours to a week. Depending on the specific type of patch used, the drug delivery surface area may be the entire lower/adhered surface of the patch, or may comprise a surface area that is less than the total surface area of the lower surface of the patch.

In preferred embodiments of the invention, the transdermal patch is a conductive transdermal patch. Although suitable for independent use to effectuate delivery and controlled transdermal absorption of at least one drug comprised therein, when used in conjunction with the provided ultrasound device to further facilitate application of SAW to the transdermal patch and skin surface, optimal results can be achieved. Specifically, application of surface acoustic waves (SAW) with the portable ultrasound device through the transdermal patch impregnated with therapeutic agent(s) as described herein results in optimal transdermal absorption of the therapeutic agent(s). As discussed in more detail below, the SAW-generating system comprising the transdermal patch as described herein provides for enhanced transdermal delivery of a wide variety of drugs, including, e.g., a *cannabis* drug as described herein with respect to specific embodiments of the invention. In specific embodiments, the system comprises a portable ultrasound device coupled to a transdermal patch, wherein the ultrasound device is Applicant’s PAINSHIELD device.

The SAW-activating (or SAW-generating) system described herein addresses current concerns and complications with topical and transdermal drug applications. Specifically, the use of SAW in the described system and according to the described methods results in improved permeation of a pharmaceutical composition comprising a therapeutically effective amount of a *cannabis* drug and optionally one or more additional drug(s)) due to elliptical motion of particles during micro-vibrations on the surface of the transdermal patch.

Furthermore, embodiments of the present invention relate to a system and methods of applying therapeutic ultrasound energy in the form of SAW in combination with and to enhance transdermal delivery and absorption of therapeutic agents to treat or alleviate symptoms associated with a disease or condition of a subject. The ultrasound energy emitted by the system described herein is effective to penetrate deep into the tissue of the subject and is not limited to application of surface ultrasound energy. In certain embodiments, applying the ultrasound energy to a surface of the skin is furthermore effective to alleviate pain in tissue of the subject.

A portable ultrasound device suitable for use in the present invention is described in U.S. Pat. No. 9,199,096, the contents of which are incorporated by reference herein. Such portable ultrasound device preferably comprises: an energy generating module configured to generate a driving signal that can be transformed into ultrasonic energy, wherein the energy generating module comprises a power source, an oscillator, a driver component, and a sensor; and an ultrasound transducer comprising a piezoelectric component and optionally a lens component. The transducer is configured to receive the driving signal from the energy generating module, to transform the driving signal into ultrasonic energy, and to control a direction of the ultrasonic energy emitted from the ultrasound transducer.

A transducer suitable for use in embodiments of the present invention is also described in U.S. Pat. No. 9,492,687, the contents of which are incorporated by reference herein. That is, a transducer suitable for use in embodiments of the invention is the THERASONX transducer, which has been approved by the FDA for USP Class 6 and has passed cytotoxicity testing. The prior cytotoxicity tests provide a level of safety insurance for biocompatible devices that may be implanted. The transducer of THERASONX is made from a lead-based piezoelectric ceramic that is typical of most therapeutic ultrasound systems. To protect the subject and the piezoelectric component, the piezoelectric is completely housed in a waterproof biocompatible shell consisting of a lens, ring housing, and boot. Other transducers may also be used in the portable ultrasound device; however, "low-profile" ultrasound transducers having a profile not greater than about 6 centimeters in height are preferred.

In embodiments, the portable ultrasound system described herein enables application of SAW, from a compact (handheld) platform, for a range of medical and non-medical applications. This furthermore allows for a greater mobility of the subject. The portable ultrasound device is not only suitable for all-day use, but is convenient and designed for all-day use. Additionally, the portable ultrasound system of the present invention produces ultrasound energies covering therapeutic physiotherapy and drug delivery power ranges and frequencies, while the transducer is small enough to be placed inside a transdermal patch for application of ultrasound.

The portable ultrasound system of the invention provides for a wide range of ultrasonic beams and wave patterns, enabling a wide range of applications. The system, as used in methods of the invention descried further herein, can be used virtually for any region to which a subject may desire to apply ultrasound at preferred frequencies of 0-40 MHz.

Referring now to FIG. 1, provided is a drawing of a portable ultrasound system 100 used in embodiments of the invention. The system 100 includes an energy generating module 300 that connects to an actuator 400 with a cable 330. The energy generating module 300 may be powered with a built-in rechargeable battery, and may comprise a screen display 310. The actuator 400 contains an ultrasonic transducer 500, which is the active component that converts electric signals from the energy generating module 300 to ultrasound waves. In preferred embodiments, the ultrasonic transducer 500 is a miniature transducer that transmits low-frequency, low-intensity ultrasound through skin and flexible materials surfaces.

The actuator 400 comprising the ultrasonic transducer 500 is incorporated into a transdermal patch 600 that comprises an adhesive layer 620 on at least a portion or a perimeter of an outer surface thereof (i.e., surface facing the skin). For effective treatment, the ultrasonic transducer 500 should preferably face the outer surface of the transdermal patch 600 (i.e., to face the adhesive layer 620) such that, upon adherence of the transdermal patch 600 to a subject's skin, the ultrasonic transducer 500 is in full contact with the subject's skin.

Figure 2A:
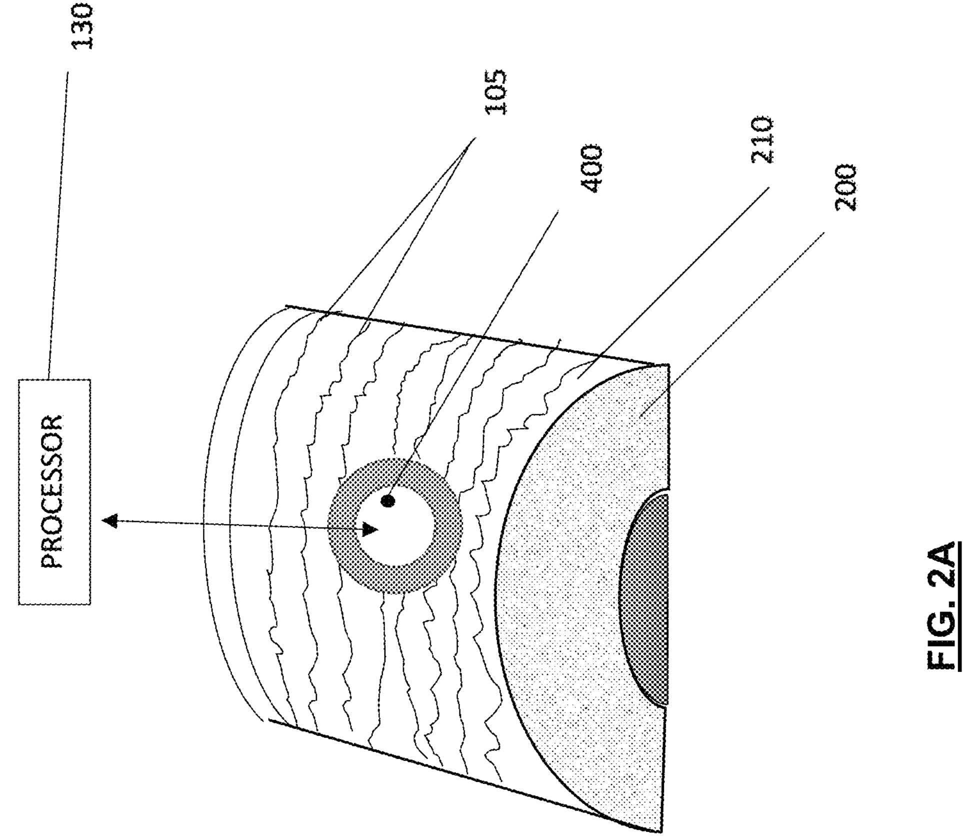
FIG. 2A is a schematic illustration of an actuator for producing surface acoustic waves positioned on an external surface portion of a subject's skin, in accordance with embodiments of the invention.

Pursuant to embodiments of the invention, FIG. 2A shows an actuator 400 for producing surface acoustic waves positioned on an external surface 210 of a subject's skin 200. Actuator 400 is in electrical communication with a processor 130. The processor 130 may be, for example, a central processing unit (CPU), and may include an oscillator, an amplifier, and any other component(s) used for receiving and transmitting signals and making calculations related to the received and transmitted signals. Upon receipt of an electrical signal from the processor 130, actuator 400 is capable of generating high frequency mechanical vibrations, in a range from KHz to MHz. These high frequency mechanical vibrations create surface acoustic waves (SAW) 105 (in the nanometer range) on the external surface 210 of the skin 200, and also penetrate into some of the deeper layers of the skin 200. The frequency of generated mechanical oscillations in actuator 400 is directly related to the frequency produced by processor 130. Thus, for example, if oscillations are in the MHz range the mechanical vibrations will also be in the MHz range, and similarly for other ranges. The energy source applied via processor 130 may have a periodical or non-periodical character and may be electromechanical, electromagnetic, or electro-optical.

In embodiments, actuator 400 may be comprised of one or multiple piezoelectric transducers, one or more electromagnetic acoustic transducers, or one or more laser pulse transducers. In the case of piezoelectric and electromagnetic transducers, direct contact between the actuator 400 and a subject's skin is necessary, whereas non-contact methods may be employed when using laser pulse transducers.

Figure 2B:
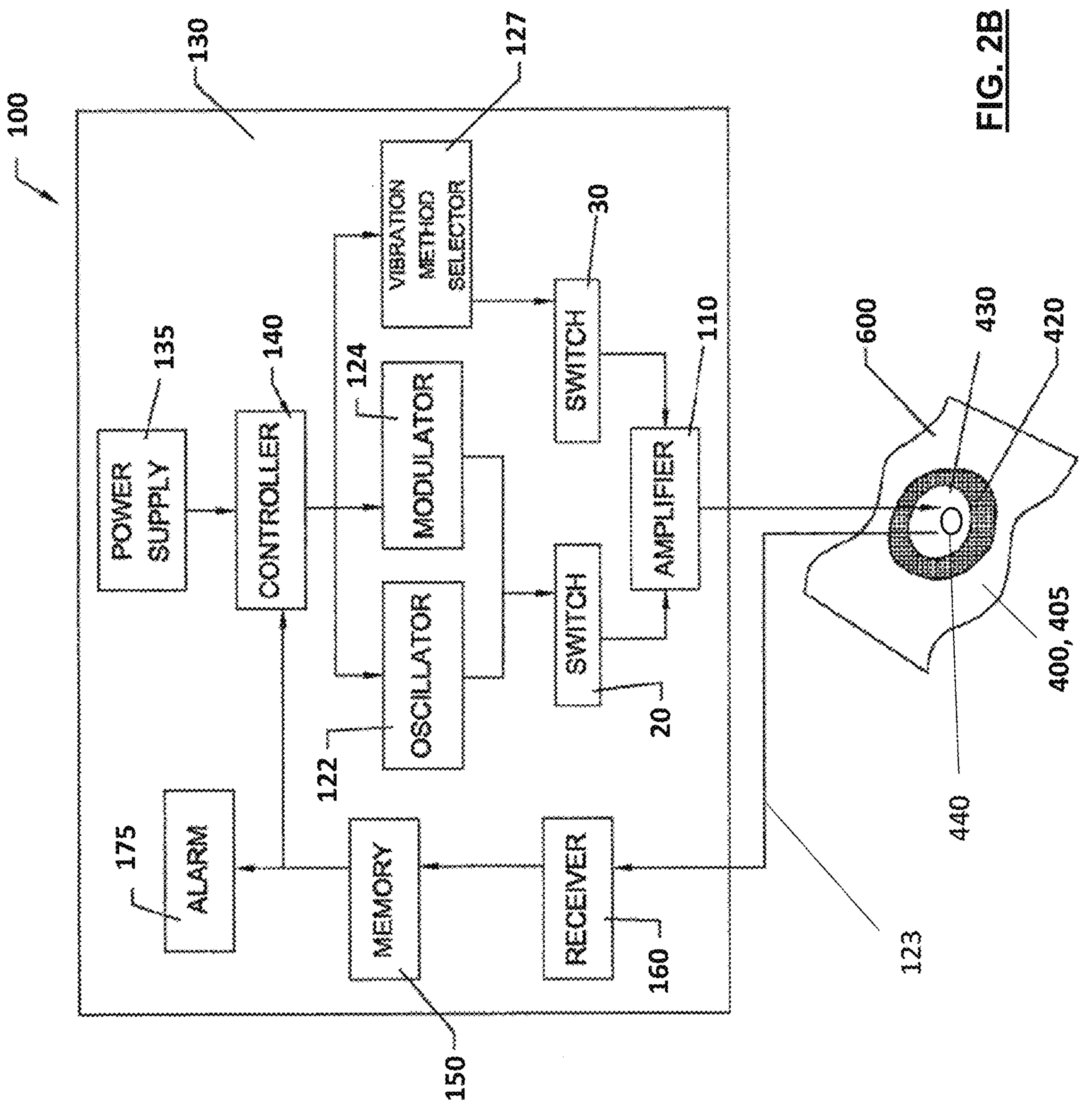
FIG. 2B is a block diagram illustration of a system for treating skin using SAW, in accordance with embodiments of the invention.

Provided in FIG. 2B is a block diagram illustration of a system 100 for treating skin with surface acoustic waves (SAW) according to embodiments of the invention. The system 100 creates SAW 105 via actuator 400, which is a piezoelectric actuator 405. However, as noted below and as would be understood by persons skilled in the art, other methods may be used to create SAW, including electromagnetic stimulation and laser pulse excitation. System 100 includes an actuator 400 comprised in a transdermal patch 600, the actuator 400 having an activating portion 480 and an electrode portion 430. The system further includes a processor 130 in electrical communication with electrode portion 430 of actuator 400. In embodiments, actuator 400 is a piezoelectric actuator 405 and works by converting electrical signals from processor 130 into mechanical energy, wherein the mechanical energy is transmitted to skin and creates SAW 105 on surfaces thereof. In some embodiments, actuator 400 is configured to transmit electrical signals proportional to the mechanical energy created by processor 130, and thus may provide a feedback loop 123 to regulate the electrical signals produced by processor 130.

Processor 130 includes a power supply 135 for providing electrical energy to the system 100. In some embodiments, power supply 135 is a separate unit (such as a power cord), and in some embodiments the power supply 135 is incorporated into the processor 130 (such as a battery). Processor 130 further comprises a controller 140 for controlling output parameters of the processor 130. Controller 140 is in electrical communication with an oscillator 122 for providing signals at various frequencies, a modulator 124 for modulating parameters such as frequency, amplitude, etc., and a vibration method selector 127 for providing different types of vibrations, such as single-phase, two-phase or multiphase vibrations. Oscillator 122 and modulator 124 are connected to a first switch 20 for selection of signal parameters. Vibration method selector 127 is connected to a second switch 30 for selection of a vibration method. The selected signal of the selected vibration type is sent through an amplifier 110 to actuator 400.

In embodiments where electrical signals are sent from actuator 400 to processor 130, the signals are received by a receiver 160 within the processor 130. In some instances, signals may be sent by a separate sensor 440 placed on or near or incorporated within actuator 400. Signals received by receiver 160 are sent to a memory module 150 where they are compared with expected values. Results of the comparison are then either sent to controller 140, where signal parameters (such as amplitude and frequency) may be automatically adjusted based on information received or sent to an alarm 175 for alerting a user that parameters should be adjusted manually.

In embodiments of the invention, propagation of Lamb waves depends on density, elasticity, and other material properties of the solid, such as, e.g., the skin, and they are influenced a great deal by the selected frequency and material thickness. With Lamb waves, a number of modes of particle vibration are possible, but the two most common are symmetrical and anti-symmetrical. The complex motion of the particles is similar to the elliptical orbits for surface waves. The presence of, specifically, SAW on internal and external surfaces of skin causes a pushing/pulling effect of materials on these surfaces, including fluids and particulates suspended therein. There are several methods for producing SAW on skin, including electromagnetic, laser pulses, or piezoelectric methods, as will be discussed in greater detail below.

Figure 3A:
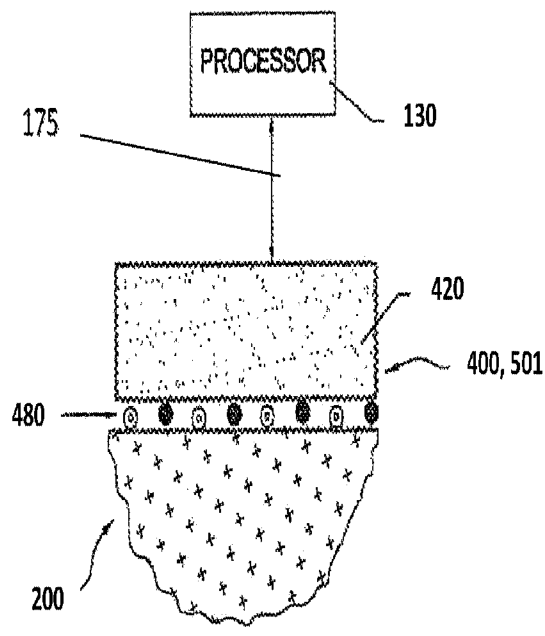
FIG. 3A is a diagrammatical illustration and FIG. 3B is a schematical illustration of skin with an actuator attached thereto, wherein the actuator comprises an electromagnetic transducer.

In reference to FIG. 3A, illustrated is a cross-sectional view of a subject's skin 200 with an actuator 400 attached thereto so as to interface the skin 200 or to be in contact with the skin 200. In the depicted embodiment, actuator 400 comprises a base portion 420 that interfaces the skin 200 and an activating portion 480 operably coupled to the base portion 420. The base portion 420 may be of any conductive material, such as, e.g., a metal, and the activating portion 480 comprises electromagnetic transducers 501, such as electromagnetic ultrasound transducers available from Olympus Company, Panametrics-NDT Ultrasonic Transducer. In certain embodiments, the base portion 420 may be the face of the electromagnetic transducer 501.

In embodiments, activating portion 480 of the actuator 400 is configured to excite Lamb waves in plates. This type of actuator 400 vibrates the atoms within the skin 200. Specifically, processor 130 is in electrical communication with and applies current to the base portion 420, which is comprised of an electrically conductive material. When the current is applied at a particular ultrasonic frequency, activating portion 480 creates vibrations of Lamb wave type, and the distance between maximum amplitudes will be equal to one-half the wavelength of SAW excited on the skin 200.

Figure 3B:
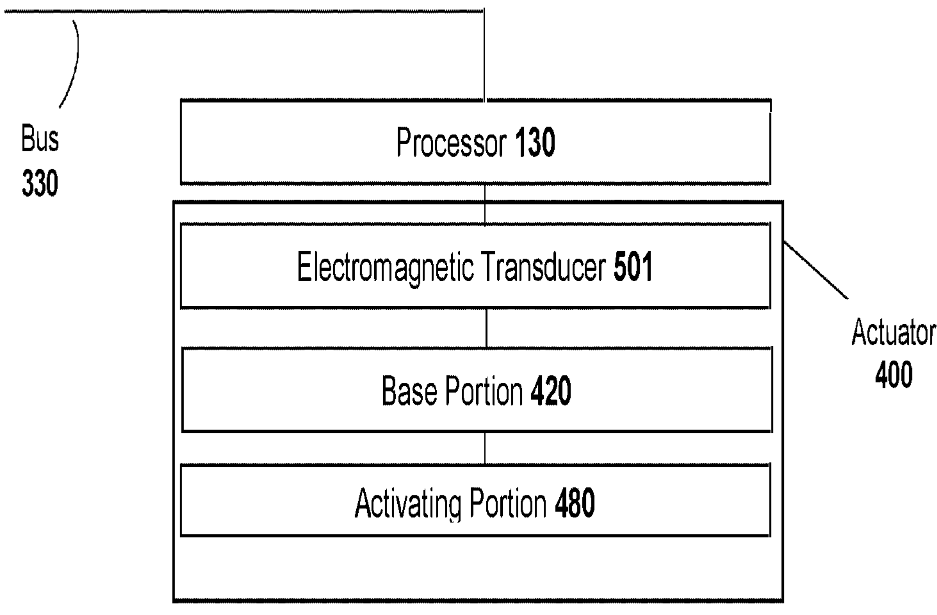

FIG. 3B is a diagrammatic illustration of embodiments encompassed by FIG. 3A. As shown in FIG. 3B, actuator 400 is comprised of electromagnetic transducer 501, a base portion 420, and an activating portion 480. The base portion 420 of the actuator 400 is in electrical communication with a processor 130 that applies a current thereto.

Figures 4A, 4B:
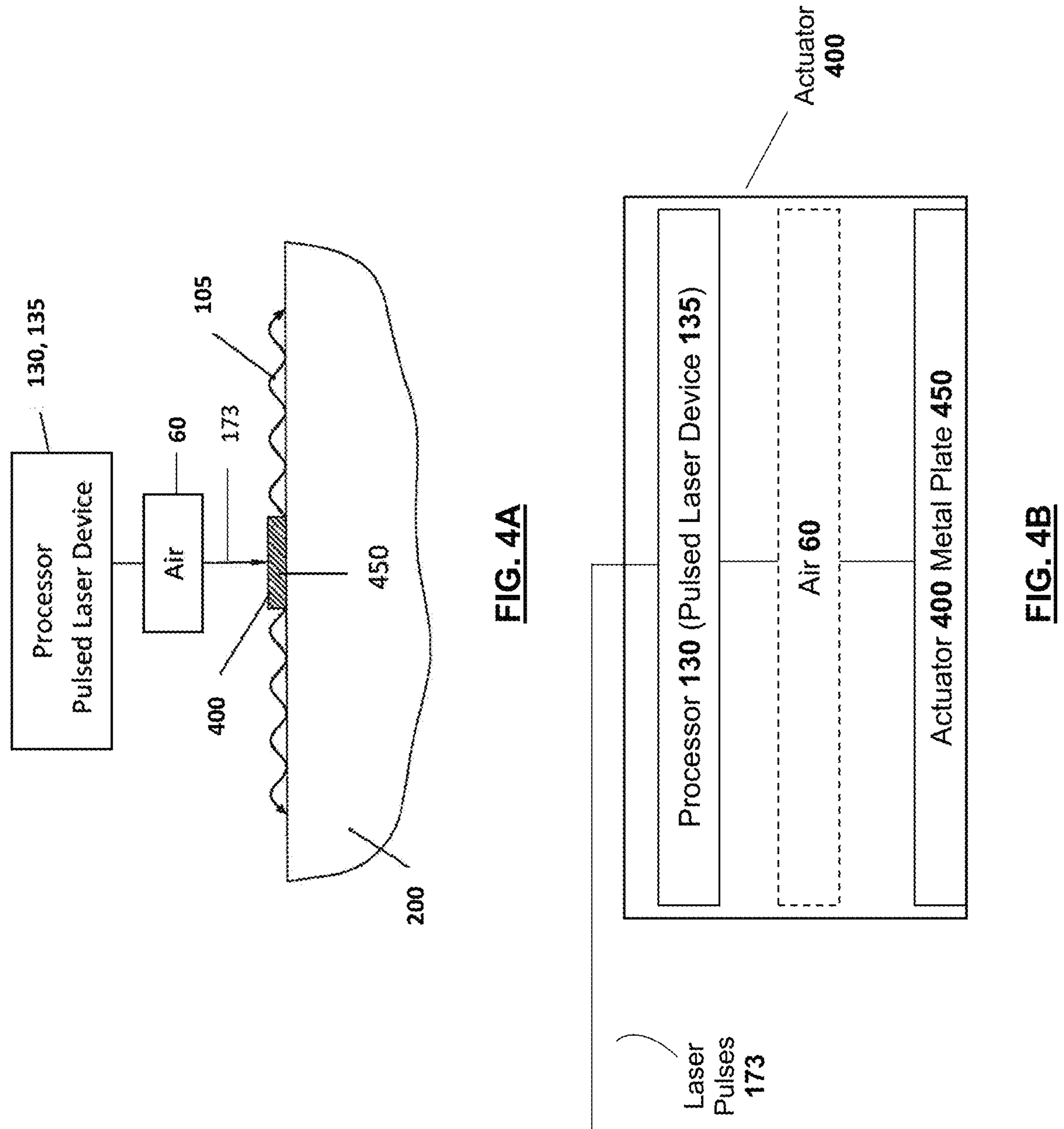
FIG. 4A is a diagrammatical illustration and FIG. 4B is a schematical illustration of skin with a processor, wherein the processor is a pulsed laser device.

In reference to FIG. 4A, provided is an illustration of another embodiment of the invention wherein the processor 130 is a pulsed laser device 135. Actuator 400 comprises a metallic plate 450 configured to vibrate in response to laser pulses 173 emitted and communicated by the processor 130 (pulsed laser device 135). In this embodiment, no contact is necessary between actuator 400 and processor 130 since laser pulses 173 travel through the air 60. Pulsed laser device 135 is used to generate SAW 105 in solids by a thermoelastic mechanism, wherein the resulting elastic displacement waveform has a wide band.

The frequency range of excited SAW using pulsed lasers has a limited bandwidth as only short pulse widths can be excited in solids with a pulsed laser device. The amplitude and frequency bandwidth of the pulsed laser device 135 induced SAW 105 are improved by decreasing the radius of the focused laser spot. For example, a laser pulse 173 focused to a line produced by Max-Planck-Institute for Solid State Research may be applied.

FIG. 4B provides a diagrammatic illustration of embodiments of the invention encompassed by FIG. 4A, wherein processor 130 is a pulsed laser device 135. As shown, the actuator 400, which is a metal plate 450, is communicably coupled to the pulsed laser device 135. Since laser pulses 173 emitted from the pulsed laser device 135 are able to travel through air 60, the actuator 400 (metal plate 450) does not have to be in contact with the processor 130 (pulsed laser device 135).

Figures 5A, 5B, 5C:
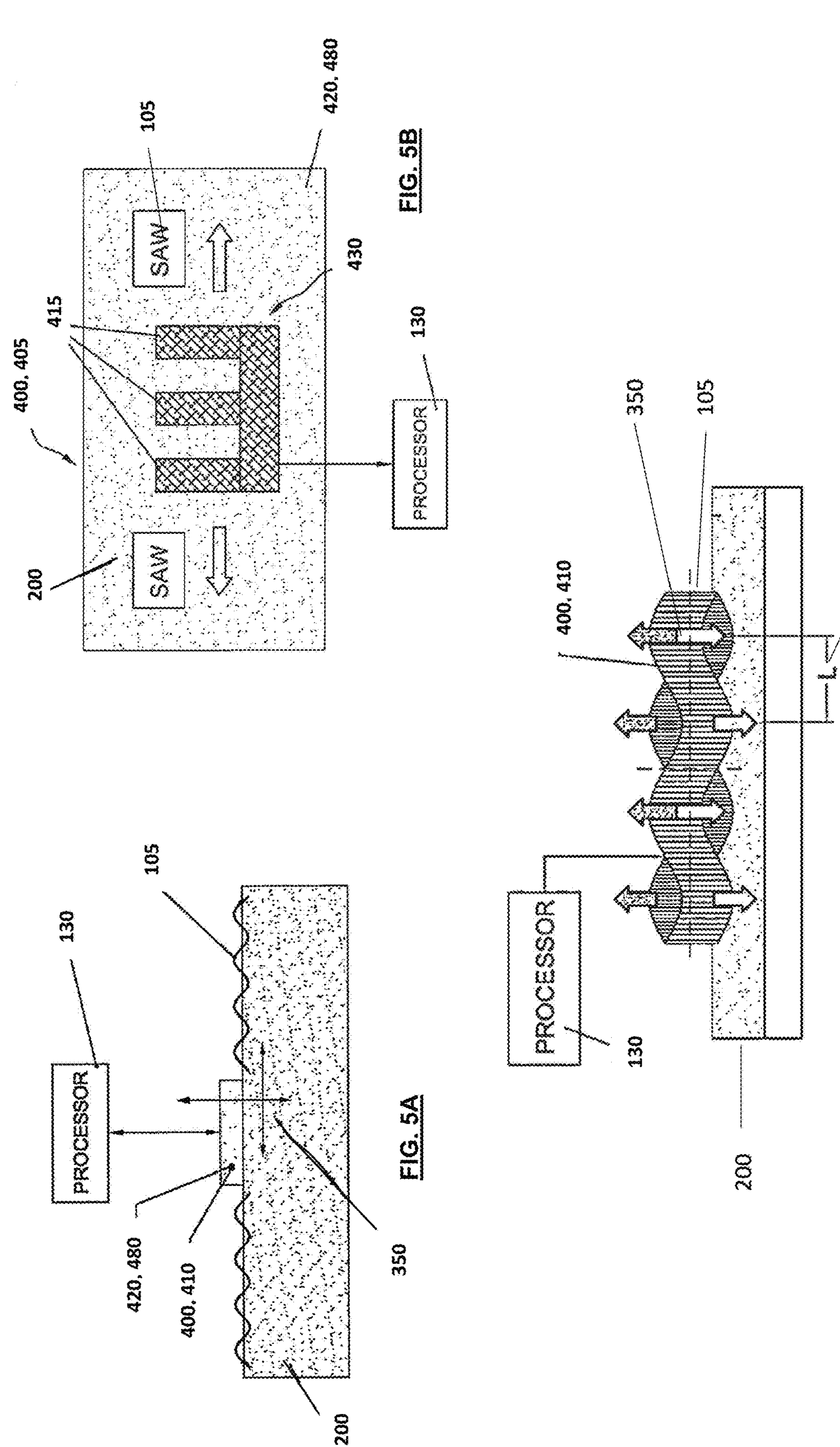
FIGS. 5A-5C are schematic illustrations of a transdermal patch comprising a transducer according to three separate embodiments of the invention.

Reference is now made to FIGS. 5A-5C, which provide illustrations of an actuator 400 comprising one or more piezo elements 410 configured to provide SAW. The piezo elements 410 are configured to provide vibrations at amplitudes of between 0.1 to 4 nm, preferably from 0.5 to 1.5 nm. In these embodiments, actuator 400 may include a base portion 420 and an activating portion 480, wherein activating portion 480 is comprised of the piezo elements 410. The piezo elements 410 include electrodes, which are not shown as they may be placed in any location, and different possibilities for positioning of electrodes are known to those skilled in the art. In some embodiments, base portion 420 is also the activating portion 480 and, thus, comprises the piezo elements 410.

In an embodiment shown in FIG. 5A, actuator 400 is comprised of a base portion 420, wherein base portion 420 is a piezo element 410, and thus acts as an activating portion 480. In some embodiments, multiple piezo elements 410 may be used. Actuator 400 may work in thickness and/or radial vibration modes, thus generating SAW 105 on surfaces of skin 200. The vibrations 350 of piezo element 410 occur in two planes, as depicted by arrows.

Shown in FIG. 5B, actuator 400 is an integrated piezotransducer, also known as an interdigital transducer (IDT), 405. The integrated piezotransducer (IDT) 405 has multiple elongated portions 415 or fingers, generating SAW 105 on surfaces of skin 200 when the distance L between two of the elongated portions 415 is proportional to one-half the length of the SAW 105. The interdigital transducer 405 comprises a base portion 420 which also may act as activating portion 480. Activating portion 480 comprises a piezoelectric material with an electrode portion 430 sprayed thereon in a particular configuration, such as, e.g., the "W" configuration shown in FIG. 5B.

The configuration shown in FIG. 5B represents three suitable setups for the interdigital transducer 405 according to embodiments of the invention. In one embodiment, base portion 420 is comprised of a piezoelectric material and acts as an activating portion 480, with electrode portion 430 sprayed thereon in a "W" configuration as shown, or in any known configuration for IDT. In another embodiment, base portion 420 is comprised of a material that is not piezoelectric, and activating portion 480 and electrode portion 430 are both configured in a "W" configuration as shown, or in any known configuration for IDT. That is, the shape of the piezoelectric material of an activating portion 480 matches the shape of the electrode 430. In a third embodiment, activating portion 480 and electrode portion 430 are both configured in a "W" configuration as shown or in any known configuration for IDT, and are placed directly on a surface of the skin 200. Thus, base portion 420 is activating portion 480, both of which have a particular configuration which is the same as electrode portion 430 and is suitable for use as an IDT. Electrode portion 430 faces away from the skin 200, and base portion 420 and/or activating portion 480 is coupled to skin 200, either directly or with the use of a matching layer.

In all of the above-described configurations encompassed by FIG. 5B, electrode portion 430 is in electrical communication with processor 130. When a voltage is applied to electrode portion 430 via processor 130, then a thickness vibration is initiated in activating portion 480 and Lamb waves are initiated by a resonance effect. The energy distribution from the vibrating elements is in two opposite directions shown by the arrows. The distance L between elongated elements 415 is equal to half the wavelength of SAW 105 which is excited with this method. The electrode portion 430 typically has a configuration that concentrates the created energy in the surface layer up to 100μ. In embodiments, the number of electrode elements 415 of the electrode portion 430 can vary depending on the desired amplitude of the SAW 105. In certain embodiments, the elongated elements 415 of the IDT 405 can be excited with a magnetic or laser means.

Many alternative configurations for electrode portion 430 are possible and are known in the art. For example, two electrode portions may be positioned facing each other such that elongated portions of one interlock with elongated portions of the other, with gaps therebetween. The electrical voltage is applied to both electrode portions and the direction of SAW propagation is in two directions. In other embodiments, a continuous electrode may be used. The distance between the elongated portions is equal to $\lambda_a$, i.e., the wave transits the distance between each pair of electrode elements precisely by the time equal to the phase of the exciting signal. Thus, the SAW intensity is proportional to the number of pairs of electrode elements. In still another embodiment, the electrode portion 430 includes two external active electrodes and multiple passive electrodes positioned between the active electrodes. By varying the number of passive electrodes, it is possible to change the width of the frequency range to change resistance of radiation $N^2/4$ times, where N is the number of passive electrodes.

Reference is now made to FIG. 5C, which is an illustration of an actuator 400, such as the actuator 400 shown in FIG. 5A, during vibrations 350. Actuator 400, after activation by processor 130, begins to vibrate in two directions—up and down—as shown by gray and white arrows, respectively. Vibrations of piezo element 410 generate SAW 105 on an external surface of skin 200 when a distance L 115 between two maximal amplitudes of bending vibration modes are proportional to one-half the length L of the SAW 105. In this embodiment, piezo element 410 is configured to work with symmetrical Lamb vibration modes, which works similarly to the interdigital transducer (IDT) 405 shown in FIG. 5B. That is, the standing wave maximal amplitudes created in a thin plate are similar to elongated portions 415 of the IDT 405 (FIG. 5B), creating elastic deformations in the surface of skin 200 and exciting SAW 105 thereon. In some embodiments, a coupler may be positioned between actuator 400 and skin 200. For example, an adhesive or glue layer for attaching the actuator 400 to skin 200 may be used, wherein the glue layer has a smaller acoustic velocity than piezo element 410 but a larger acoustic velocity than skin 200.

In embodiments of the invention, the actuator includes a base portion in contact with the skin of a subject and an activating portion to which voltage is applied by a processor, which may include a power supply. The voltage from the processor excites elastic volumetric (three dimensional) vibrations in the activating portion, which are transmitted to the base portion, resulting in production of surface acoustic waves (SAW) in two opposite directions along the skin surface. In some embodiments, the base portion is comprised of piezoelectric material; in some embodiments, only the activating portion comprises piezoelectric material. In certain embodiments, when the base portion of the actuator is comprised of piezoelectric material, the base portion acts as the activating portion.

According to embodiments of the present invention, one method for achieving SAW is by summation of SAW from two actuators placed at an angle relative to one another on the surface of a subject's skin. Running-type waves excited and transmitted by each of the actuators (in the directions of their respective placement angles) intersect and thus interfere with each other, resulting in standing waves being formed on the surface of the skin. As the interferences of the waves in the areas of overlap concentrate acoustic energy, it is possible to create a concentrated SAW effect by strategic placement of the actuators.

In embodiments of the invention, two (or more) actuators may be connected to one processor, or separate processors may be used for each actuator. For example, a first actuator in electrical communication with a first processor and a second actuator in electrical communication with a second processor may be placed at different locations on the skin. In such embodiments, the relative placement of the actuators remains relatively constant, but the overall positioning may be changed as necessary.

In still further embodiments, a focused effect of SAW standing waves can be created by using actuators placed in a circular configuration. Specifically for IDT actuators, which tend to crate weak SAW, it may be advantageous to focus energy concentration by placing a series of IDT actuators in a circular configuration. In doing do, running waves propagating to the center of the circular configuration will interfere with each other in the center, thus creating an area of standing waves with much higher acoustic power. Due to the focusing effect of standing waves, the pressure greatly increases in the central area.

A focused effect as the one described above, can also be obtained using a ring-shaped piezo element for the activating portion of the actuator. In such embodiments, running waves are directed inwardly towards a center of the ring-shaped piezo element. Interaction of these running waves with one another cause formation of standing waves at the center. The minimal thickness of a ring-shaped piezo element for this purpose may be in the order of 0.05 mm to 0.5 mm, preferably from 0.05 mm to 0.1 mm. The inner radius of the ring-shaped piezo element may be in the order of 1-100 mm. In some embodiments, the ring-shaped piezo element has an outer layer, which may be, e.g., of an absorbing material, such as rubber, silicone, polymer, or metal, or any other suitable absorbing material. The absorbing material of the outer layer may be adapted to absorb acoustic vibrations that are directed outwardly from the ring. Pursuant to other embodiments of the invention, a power supply system may be adapted to supply electrical input to the ring-shaped piezo element of the actuator. The frequency of the electric input may be selectively controlled. Electric input from the power supply may be delivered to the conductive material of the ring-shaped piezo element to cause it to substantially vibrate. For example, the electric input delivered to the ring-shaped piezo element may cause thickness, longitudinal, or torsion, or any other acoustic wave form. The selected frequency is dependent on various system parameters, including (but not limited to) the thickness of the piezoceramic material used for the ring-shaped piezo element. As an example, the frequency applied to a ring-shaped piezo element having a thickness of 0.05 mm may be approximately 20 MHz and the frequency applied to a ring-shaped piezo element having a thickness of 50 mm may be approximately 0.1 MHz. In some embodiments, the ring-shaped piezo element is constructed of several arc sections, which may be excited simultaneously or sequentially, or in any other combination, resulting in lower energy assumptions with higher focused results.

Selection of parameters in embodiments of the invention depends on the use and application of system 100 to the skin, and may vary according to specific requirements thereof. Frequencies may be in a range of 0.1 Hz-10 MHz. When an interface is present, such as a cream, drug, wound dressing or the like, frequencies may be in a range of 1 KHz-20 KHz so as to provide higher energy waves that can penetrate the interface. Alternatively, higher energy may be accomplished by modulation of waves to increase amplitudes. Pulsed or continuous inputs may be used. Depending on the treatment used, the types of waves may differ as well. Microstreaming may be accomplished by a large range of wave types, with the speed of microstreaming being based on the chosen parameters. In embodiments, the speed of microstreaming may be in a range of from 1 nm/minute to 10 microns/minute.

Figure 6:
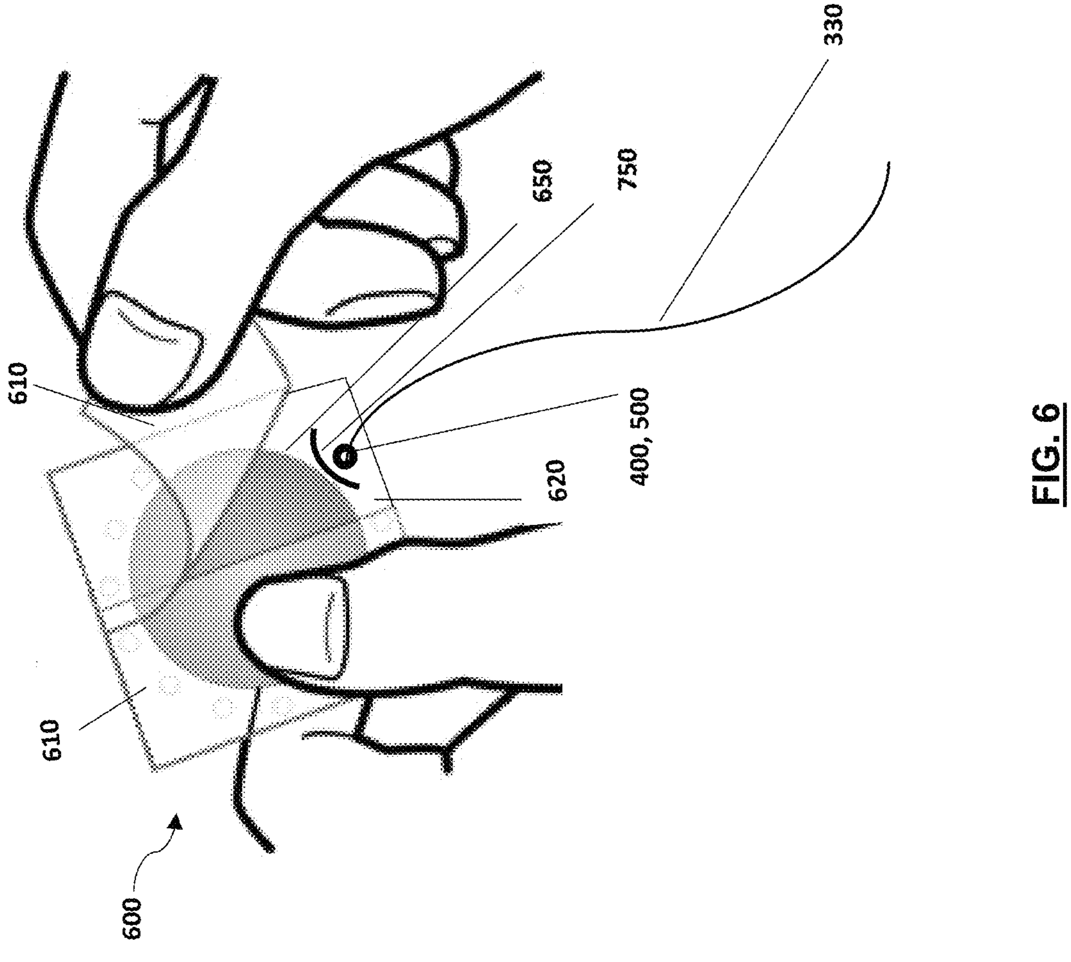
FIG. 6 is an illustration of a transdermal patch showing the placement of an actuator with a metal transducer facing in a direction of adhesion of the adhesive layer.

Reference is now made to FIG. 6, which is an illustration of a transdermal patch 600 according to embodiments of the invention. The transdermal patch 600 may be provided in various shapes and configurations. Although the transdermal patch 600 is shown as having a square shape, this is for illustration purposes only. In certain preferred embodiments, the transdermal patch has a circular shape or a rounded shape. In certain embodiments, the transdermal patch has an arch-like configuration that includes a first side and a second side. The transdermal patch can be configured to fit on specific portions of skin, or to have any other desirable shape or configuration.

In embodiments of the invention, the transdermal patch 600 has a size sufficient to accommodate the actuator 400 comprising a transducer 500 therein, as well as a therapeutically effective amount of at least one therapeutic agent for delivery, such as a preferred pharmaceutical composition comprising a *cannabis* drug. Therefore, various sizes of transdermal patches may be used in embodiments of the invention, with the size also being determined by the desired application area of the subject's skin. In certain embodiments, a transdermal patch 600 may be of a larger size, having a size ranging from 70 mm-120 mm×80-150 mm, such as from about 90 mm×about 110 mm. Even larger patches 600 having sizes ranging from about 100-200 mm×100-300 mm are also envisioned. In embodiments, transdermal patch 600 may be of a smaller size, having a size ranging from, e.g., 30 mm-70 mm×30 mm-90 mm, such as, e.g., 50 mm×50 mm, or 60 mm×70 mm.

In embodiments, the transdermal patch 600 includes an adhesive layer 620 on an exterior surface (i.e., the surface facing the skin and distant from the cavity). Any suitable dermatologically acceptable pressure sensitive adhesive that does not react chemically with the pharmaceutical composition comprising at least one *cannabis* drug or prevent passage of the cannabinoid (*cannabis* drug) through the adhesive layer can be used for the adhesive layer 620. Therefore, the adhesive material of the adhesive layer 620 can be selected from adhesive materials that allow the *cannabis* drug to pass reasonably rapidly therethrough. In embodiments where an adhesive layer 620 is provided across an exterior surface of the transdermal patch 600 (rather than, e.g., only on a portion, or on or around a peripheral edge of the exterior surface) through which the at least one *cannabis* drug has to pass through to reach a skin surface, a suitable adhesive can be chosen from adhesives that will allow the at least one *cannabis* drug to pass reasonably rapidly from the transdermal patch to the skin surface. Specific examples of suitable adhesives include, but are not limited to, polyisobutylenes, acrylates, silicone, and combinations thereof.

It is to be understood that adhesive layer 620 is but one of many suitable ways for attaching the transdermal patch 600 of the invention to the subject's skin. For example, as an alternative to using adhesive layer, a separate tape, bandage, or adhesive component could be employed to attach the transdermal patch to the subject's skin.

In preferred embodiments, the transdermal patch 600 further comprises a protective layer 610 removably disposed on the exterior adhesive surface of the adhesive layer 620 such that it can be removed prior to adhesion of the adhesive layer 620 to the skin. In embodiments, the protective layer 610 is removably disposed over the pocket of the transdermal patch comprising the actuator 400 and transducer 500, or may be configured for easy removal by a user to reveal the cavity 650 within the transdermal patch 600, and for attachment of the actuator 400 and transducer 500 therein, with the actuator being electronically connected to a portable energy generating unit or device (not shown) by, for example, bus 330. In preferred embodiments, the actuator 400 with transducer 500 is placed in an insertion pocket 750 of the transdermal patch 600 such that a metal surface of the transducer 500 is incorporated into an external surface of the transdermal patch 600. That is, the metal surface of the transducer 500 preferably faces the protective layer 610 or the area of adhesion, such that upon application of the transdermal patch to a subject's skin, the transducer is in direct contact with the subject's skin. For ease of removal, such as, e.g., by peeling, the removable protective layer 610 may be serrated into two or more separate portions, as shown.

Although not shown, the transdermal patch preferably comprises an impermeable layer forming a protective surface of an impermeable material over the upper surface thereof (opposite the surface of adhesion). The impermeable layer protects the transdermal patch, including the cavity incorporated therein, from contamination, moisture, and the like.

In certain embodiments, the transdermal patch 600 comprises a pharmaceutical composition in the adhesive layer 620 on a lower surface of the patch interfacing with the skin. Once the removable protective layer 610 (shown in the form of two strips) is peeled off, the adhesive layer 620 may be placed to interface with and adhere to a surface of a subject's skin.

In certain embodiments, the transdermal patch 600 comprises a cavity or "reservoir" 650 in which the pharmaceutical composition is stored. In some embodiments (not shown), two or more separate reservoirs may be comprised in a transdermal patch, each containing the same or a different pharmaceutical composition. In preferred embodiments, the at least one reservoir 650 comprising the pharmaceutical composition is located in proximity to the actuator 400 with transducer 500.

The transdermal patch 600 of the present invention may further comprise a viscous flowable gel disposed within the cavity, wherein the viscous flowable gel can immobilize the at least one *cannabis* drug within the cavity. Suitable gel formulations can be obtained by making the viscosity of the cavity contents sufficiently high such that they are resistant to spreading in the event of cavity rupture. As but one example, methyl cellulose in water can be used a viscosity modifier in such gel formulations. In certain embodiments, the use of methyl in combination with the at least one *cannabis* drug can be advantageous by functioning as a surface active agent to enhance the hydrophilicity of the cavity contents.

Also included in the transdermal patch may be one or more rate-controlling microporous membrane(s). In embodiments, the one or more rate-controlling microporous membranes can be made of a single-ply material or be multi-layered. Examples of materials suitable for use as the rate-controlling microporous membrane include, but are not limited to, hydrophobic microporous polypropylene or polyethylene. In embodiments, only the inner layer of the rate-controlling microporous membrane needs to be hydrophobic (in embodiments where reservoir contents are hydrophilic) or hydrophilic (in embodiments where reservoir contents are hydrophobic). Reservoir contents can be made hydrophilic by adding surface active agent, such as an anionic surfactant.

The rate of delivery of the *cannabis* drug through the rate-controlling microporous membrane into the blood stream of the subject can be varied by: varying the surface area, thickness, and composition of the membrane; by varying the composition or weight ratios of the pharmaceutical composition comprising at least one *cannabis* drug; and/or by varying the hydrophilicity of the pharmaceutical composition or cavity contents. In this manner, the dosage rate can be varied over a wide range by adjustment of various parameters of the transdermal patch, while maintaining a substantially uniform dosage rate. However, in order to minimize variations in dosage rate between different patients owing to variations in their respective skin resistance, the permeability of the rate-controlling microporous membrane is preferably less than (e.g., from 0.6-0.9 times) the permeability of the least permeable skin likely to be treated by the transdermal patch and methods of the invention.

It is to be understood that, in addition to a *cannabis* drug, other active materials or drugs can be contained in the pharmaceutical composition, or even in another pharmaceutical composition in the cavity of the transdermal patch. Depending on the configuration of the transdermal patch, delivery of the therapeutic agent or drug may be through one or more rate-controlling microporous membrane(s) or from a drug-in-adhesive layer (if the therapeutic agent or drug is incorporated into the adhesive layer).

In embodiments, such optional additional drug(s) may include opiates, analgesics, or other drugs suitable for transdermal administration according to methods of the invention and effective for treating a disease, condition, or symptoms associated therewith in a subject, such as those referenced herein.

In accordance with an object of the present invention, the transdermal patch is formulated to deliver, in a controlled manner, a steady, staggered, or fluctuating rate of a therapeutically effective amount of a drug over the useful life of the patch until the patch is removed and replaced with a new transdermal patch. The transdermal patch can be applied as a single patch or as multiple patches across multiple locations on a surface of the skin, and it may have a life span/predetermined action time ranging from minutes (e.g., 30-40 minutes) to a couple of hours, overnight, or 8 hours, to longer intervals such as 12 hours, or even 12-24 hours such as a daily-use patch. In some embodiments, the transdermal patch is configured for extended wear for up to a week.

Specifically, the transdermal patch may be configured to provide ultrasonic output of a present frequency of, e.g., 90 kHz, and a low intensity. In some embodiments, the transdermal patch used in the SAW-generating system may deliver and alternate between an Active Phase and an Idle Phase, wherein each phase can span from 15 minutes to 1 hour, or for example 30 minutes. The transdermal patch according to embodiments may also be used in a continuous therapy session of up to 8 hours, such as up to 6.5 hours, or at any time a subject would benefit from the improved transdermal application of the therapeutic agent, such as a *cannabis* drug.

In another embodiment of the invention, the transdermal patch comprises two or more drug layers. In this embodiment, two or more different drugs, or the same or different drugs but differing in concentrations or release forms (immediate vs. extended or controlled release) may be incorporated into the two or more separate drug layers. The two or more drug layers may be selected from: a drug-in-adhesive layer, a polymeric matrix layer, and/or a reservoir drug layer. In such embodiments, the two or more layers will preferably be separated by a rate-controlling microporous membrane configured to allow the drug contained in the respective layers to permeate through the transdermal patch onto a surface of the skin in a controlled and therapeutically effective rate to achieve optimal and desired transdermal absorption of the drug(s).

In the most general terms, a transdermal patch of the invention comprises a drug layer between an impermeable backing layer and an adhesive layer. Specifically, the transdermal patch may comprise a laminate of: (a) a drug layer, which may be in the form of a matrix layer comprising a therapeutically effective amount of a drug, wherein the matrix layer has a first face and a second face; (b) an impermeable backing layer contacting the first face of the matrix layer; and (c) a bioadhesive layer contacting the second face of the matrix layer. In embodiments, the matrix layer comprises at least one *cannabis* drug.

As a further objective of the present invention, provided is a transdermal patch 600 comprising a pharmaceutical composition, wherein the pharmaceutical composition is comprised in a reservoir 650 of the transdermal patch 600 and/or in a matrix configuration, such that upon activation and generation of SAW, the pharmaceutical composition drug permeates through the reservoir 650 and/or any membrane, matrix material, and adhesive layer 620 onto a surface of a subject's skin in an improved and controlled manner.

FIGS. 7A-7D illustrate various configurations of a transdermal patch 600 comprising a reservoir 650.

Depicted in FIG. 7A is a transdermal patch 600 with a reservoir system, which comprises a drug layer 706 in the reservoir 650, a rate-controlling microporous membrane 630 forming a backing surface of the reservoir 650, an impermeable layer 640 coating the transdermal patch, and an adhesive layer 620 on the backing surface which is directly applied to a skin surface. In this embodiment, contents of the drug layer 706 within the reservoir 650 (i.e., a therapeutically effective amount of a drug) permeate from the reservoir 650 onto the skin in a controlled manner set by the rate-controlling membrane 630. The drug layer 706 may be in the form of a liquid solution or suspension, optionally further separated from the skin by the adhesive layer 620. Preferably, the reservoir 650 is encapsulated in a shallow compartment molded between the impermeable layer 640 on a top surface and the rate-controlling membrane 630 on a lower surface, as depicted.

FIGS. 7B-7D illustrate various embodiments of a transdermal patch 600 with a matrix system.

Depicted in FIG. 7B is a transdermal patch 600 with a simple matrix configuration, which comprises a polymeric matrix 670 containing a drug solution or suspension in the reservoir 650, and an impermeable layer 640 coating the transdermal patch 600 and reservoir 650. In this configuration (also known as "monolithic"), the adhesive layer 620 may surround or partially overlay the polymeric matrix 670 containing the drug solution or suspension, or it may be disposed on a periphery of the outer surface of the transdermal patch 600 (facing the skin). In certain embodiments, the polymeric matrix comprises the drug as a semi-solid matrix drug layer, FIG. 7C shows a transdermal patch 600 having a single drug-in-adhesive matrix in which the adhesive layer (otherwise identified as 620) incorporates the drug, i.e., the at least one *cannabis* drug. Therefore, a transdermal patch 600 comprising a drug-in-adhesive matrix comprises a drug-in-adhesive layer 705, and an impermeable layer 640 coating an upper surface of the transdermal patch 600. In this type of transdermal patch, the drug-in-adhesive layer 705 not only serves to adhere two or more layers together, but is additionally configured to adhere the transdermal patch 600 to the skin. In certain embodiments, the drug-in-adhesive layer 705 is configured to release the therapeutic agent or dug, such as the at least one *cannabis* drug, incorporated therein. The drug-in-adhesive layer 705 may also comprise a temporary protective layer (not shown) on a lower outer surface (facing the point of adhesion) that is removable prior to adhesion of the transdermal patch to a skin surface.

FIG. 7D shows a transdermal patch 600 with a multi-layered drug-in-adhesive matrix which includes two or more drug layers 706. The matrix shown in FIG. 7D includes a first polymeric matrix 670, which could alternatively be a first polymeric matrix layer, disposed upon a second polymeric matrix 680, an adhesive layer 620 forming a lower surface of the transdermal patch to be directly applied to the skin, and an impermeable layer 640 coating an upper surface of the transdermal patch 600. In alternative embodiments (not shown), two or more polymeric matrix layers (without adhesive layer 620) or two or more drug-in-adhesive layers may be provided. Depending on the matrix material selected, one or more adhesive layers 620 may be included, and/or one or more rate-controlling microporous membranes 630 (such membrane shown in FIG. 7A). That is, the drug-in-adhesive layers or polymeric matrix layers 670, 680 may be separated by a membrane, but not necessarily. In some embodiments, one drug-in adhesive or polymeric matrix layer may contain the drug to be administered in an immediate release form, while another layer may contain the same or another drug to be administered in a controlled/extended release form. Drug release from this system will be dependent on membrane permeability and diffusion of drug molecules. The transdermal patch 600 will preferably further comprise a temporary/removable protective layer on an outside surface of the adhesive layer 620.

In embodiments, the transdermal patch can further include a viscous flowable gel disposed within the reservoir and which immobilizes the *cannabis* drug within the reservoir. Such gel formulations can be useful to reduce the likelihood of abrupt absorption of the cannabinoid in the event of sudden rupture of the reservoir and release of the cavity contents onto the skin. Suitable gel formulations can be achieved by making the viscosity of the reservoir contents sufficiently high such that they are resistant to spreading in the event of puncture. Illustratively, methyl cellulose in water can be used as a viscosity modifier in such gel formulations. In certain situations, the use of methyl cellulose in combination with the cannabinoid composition can also be advantageous in that the methyl cellulose can also function as a surface active agent to enhance the hydrophilicity of the cavity contents.

Figure 8A:
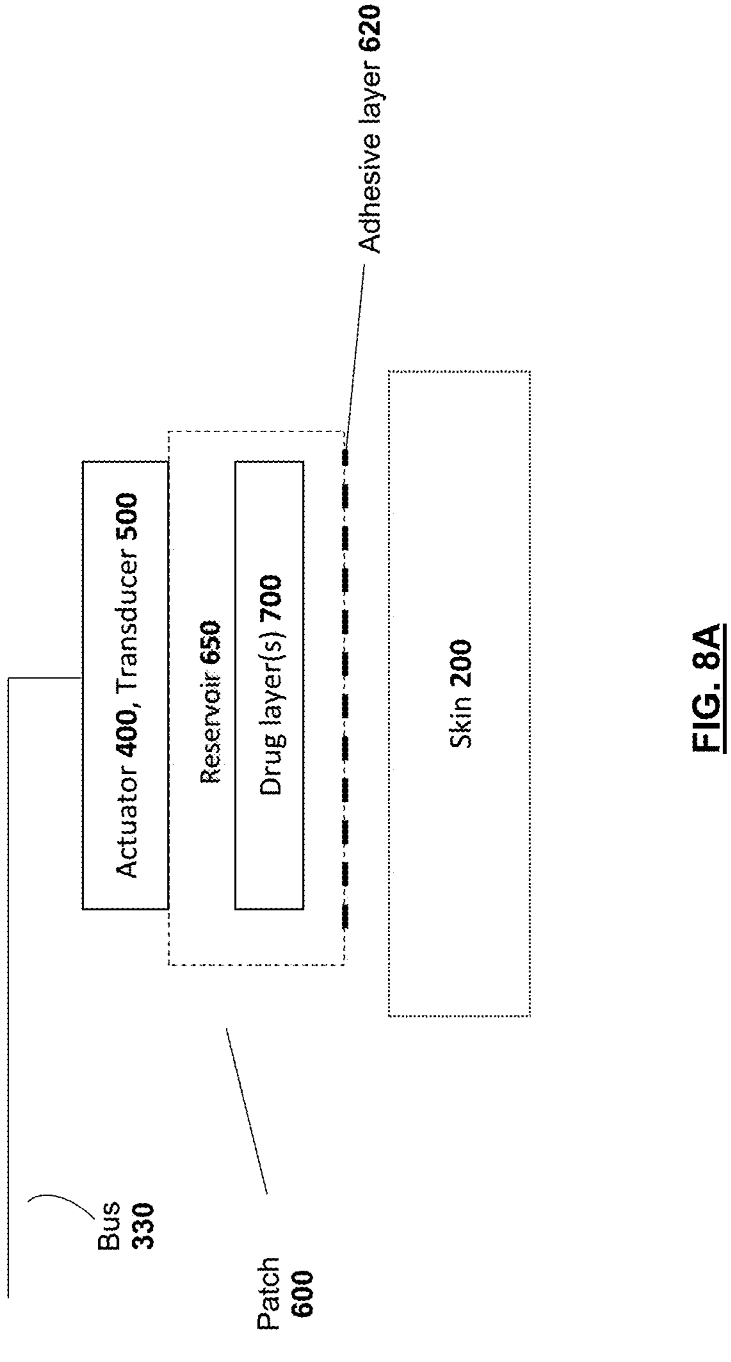
Figure 8B:
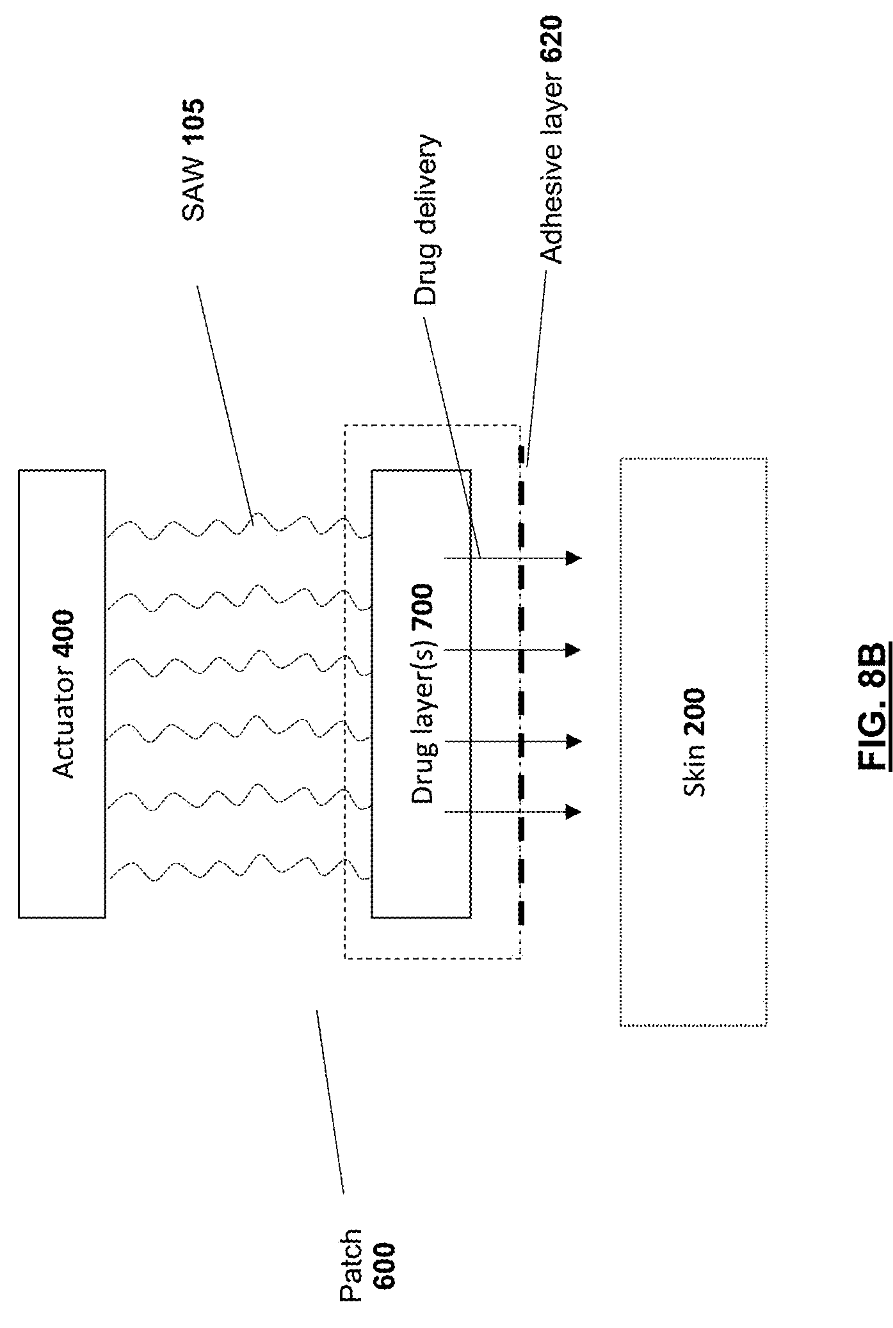
Figure 8C:
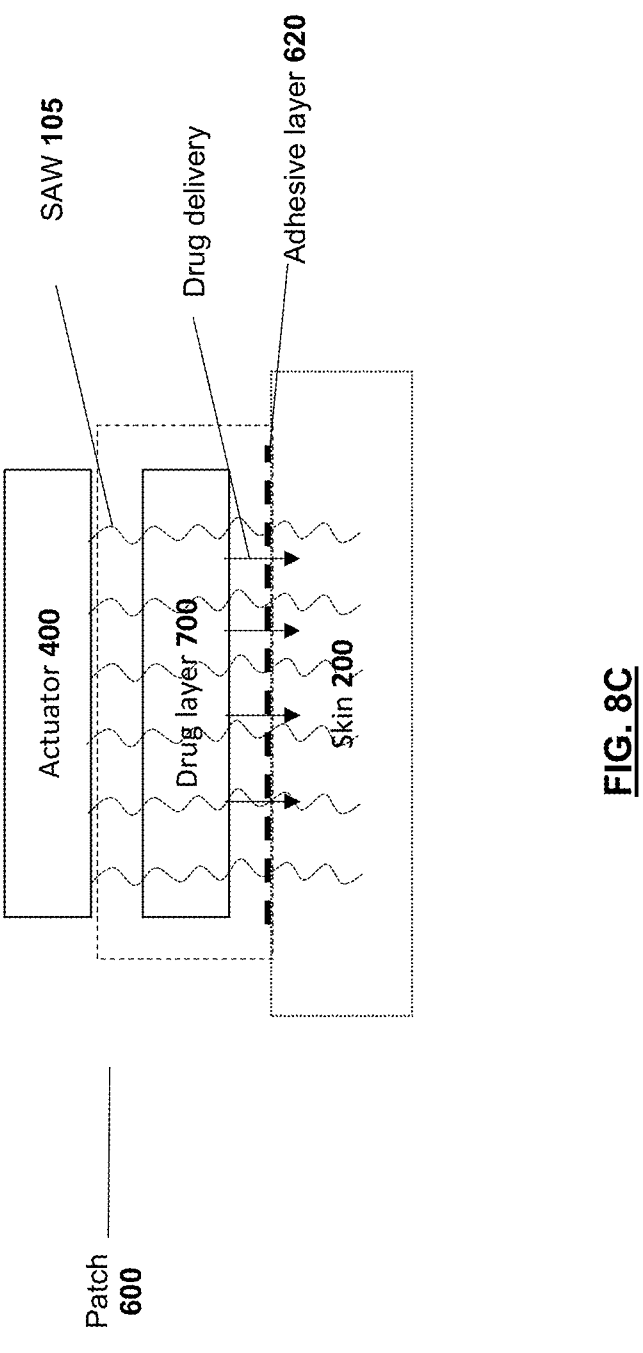

Reference is now made to FIGS. 8A-8C, which are schematic illustrations of SAW activity generated by the portable ultrasound system according to embodiments of the invention. In FIG. 8A, a transdermal patch 600 comprises an actuator 400 that comprises a transducer 500, at least one therapeutic agent, such as a *cannabis* drug, in a drug layer 700 comprised in a reservoir 650 in the transdermal patch 600, wherein the transdermal patch 600 is adhered to skin 200 by an adhesive layer 620, the adhesive layer 620 forming a lower surface of the transdermal patch 600. FIG. 8B shows transmission of SAW 105 generated by the transducer 500 through the transdermal patch 600, including the reservoir 650 comprising the dug layer(s) 700, resulting in or stimulating the flux of the at least one therapeutic agent or dug, such as at least one *cannabis* drug, of the drug layer 700 from the reservoir 650 and onto a surface of the skin 200 for absorption. In FIG. 8C, the SAW 105 generated by transducer 500 are transmitted through the transdermal patch 600. Specifically, the SAW 105 transmitted through the transdermal patch 600 also penetrate the surface of the skin 200.

In certain embodiments, the transdermal patch comprises two or more drug layers. The two or more drug layers may comprise different drugs, or the same or different drugs but differing in concentrations or release forms (immediate vs. extended/controlled release). The two or more drug layers may furthermore differ by being independently selected from: a drug-in-adhesive layer, a polymeric matrix layer, and/or a reservoir drug layer. In embodiments, the two or more layers will preferably be separated by a rate-controlling microporous membrane configured to allow the drug contained in the respective layer(s) to permeate therethrough and from the transdermal patch onto a surface of the skin in a controlled and therapeutically effective rate to achieve optimal and desired transdermal absorption of the drug(s).

Figures 9A, 9B:
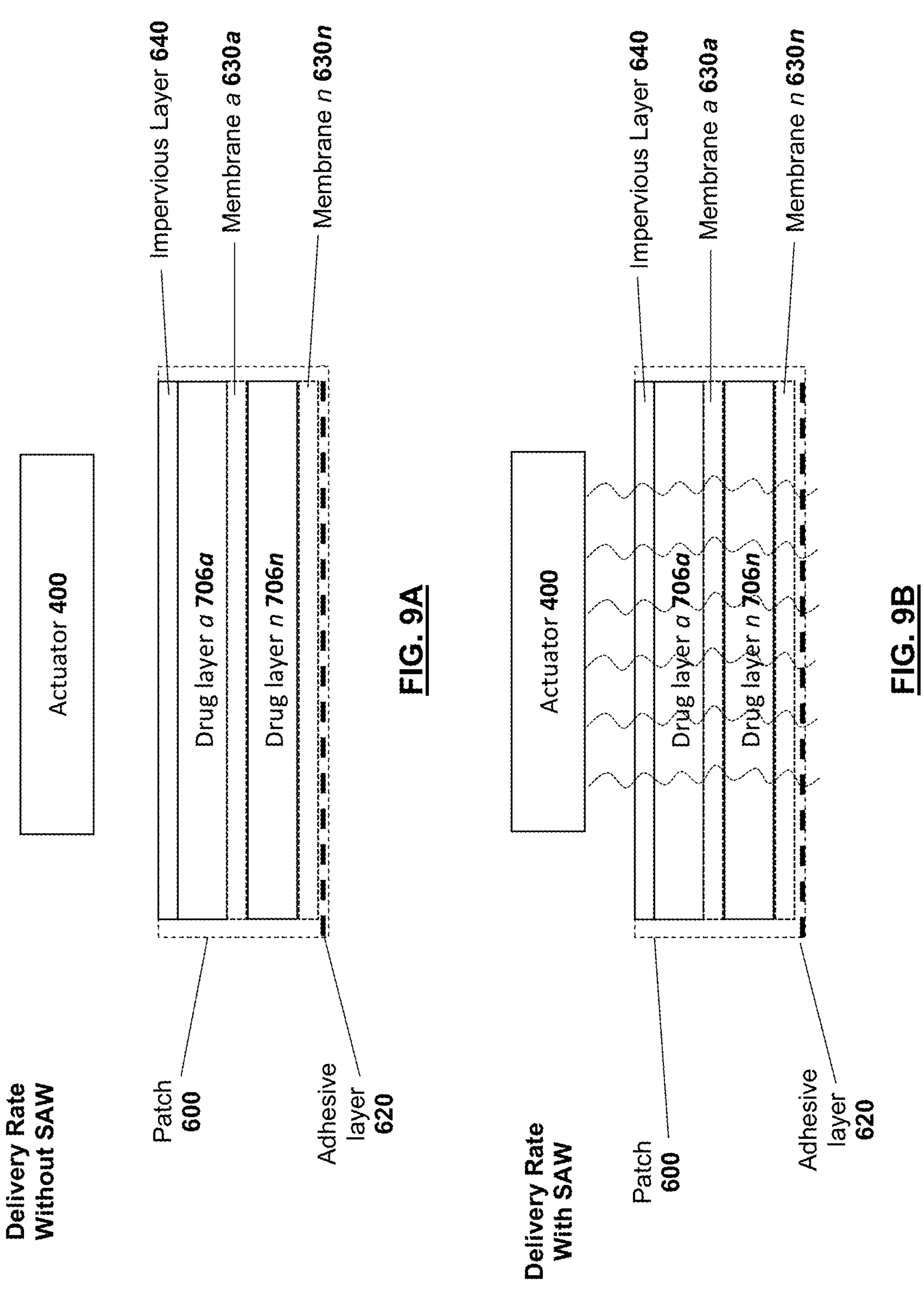
FIGS. 9A-9B are schematic illustrations of a transdermal patch with at least two drug layer membranes, with ultrasound (FIG. 9A) and without ultrasound (FIG. 9B).

A multi-layered configuration of the transdermal patch is depicted in FIGS. 9A and 9B, which show a drug layer a 706*a* provided over a drug layer n 706*n*, separated by a rate-controlling microporous membrane a 630*a*. In certain embodiments, more than two drug layers may be provided. Depending on the drug layer configuration (i.e., polymeric matrix or drug-in-adhesive), a rate-controlling microporous membrane n 630*n* may also be provided as a final layer of the configuration. Unless the final drug layer is a drug-in-adhesive layer, a separate adhesive layer 620 is included on a lower surface of the transdermal patch 600 to adhere the transdermal patch 600 to the skin surface.

In further reference to FIGS. 9A and 9B, delivery of the at least one *cannabis* drug (and optionally one or more additional drug(s)) from the transdermal patch 600 to the surface of the skin is shown without SAW (FIG. 9A) and with SAW (FIG. 9B) due to activation of the energy generating unit.

Figures 10, 11:
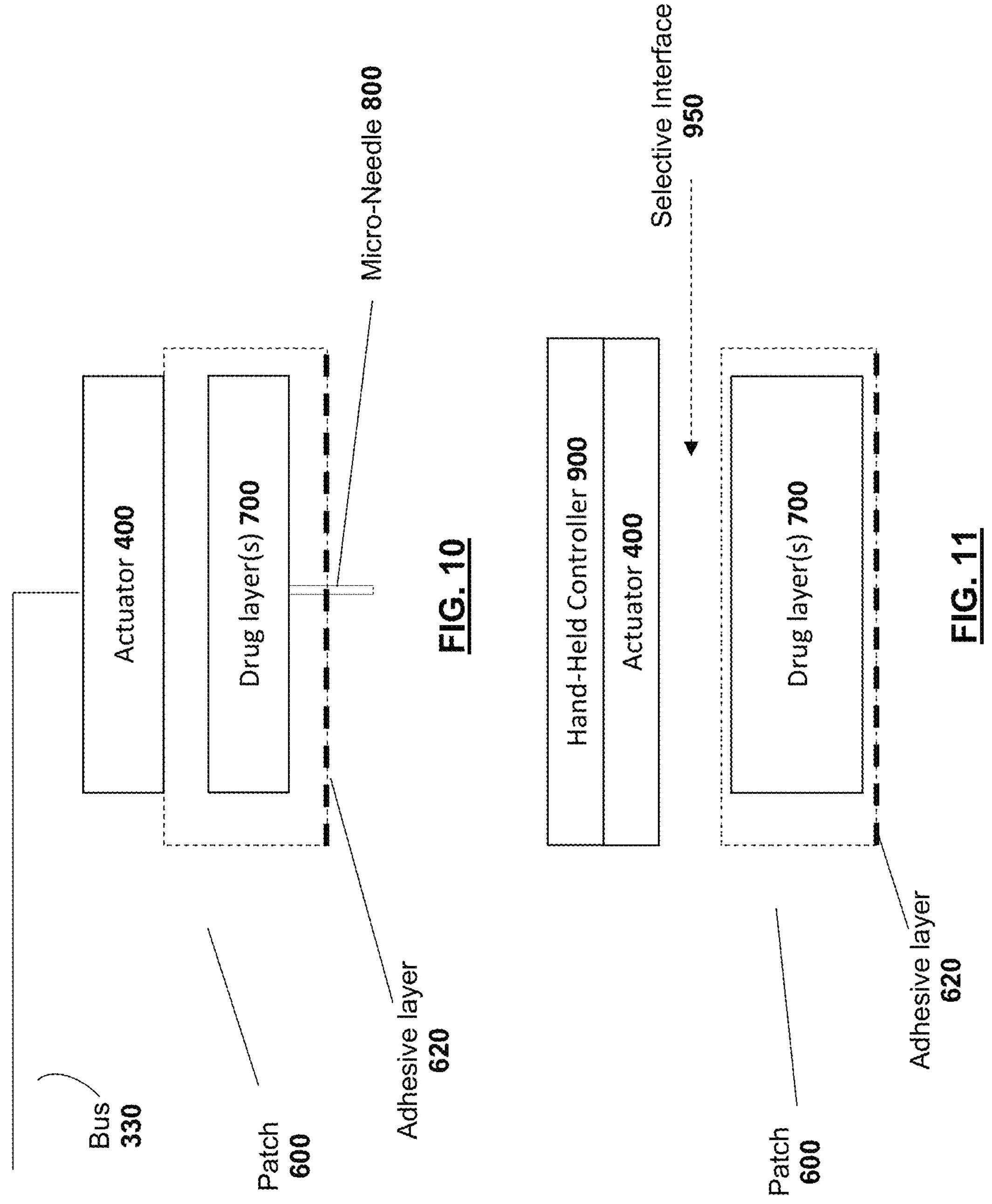
FIG. 10 is a schematic illustration of a transdermal patch according to an embodiment of the invention, wherein the transdermal patch comprises an actuator which further comprises a transducer in contact with a drug stored therein, and a microneedle penetrating the lower surface of the transdermal patch for more direct transdermal delivery of the drug into a subject's bloodstream.
FIG. 11 is a schematic illustration of a transdermal patch as described herein, however with an actuator comprising a transducer provided in a separate portable or hand-held device.

In some embodiments, a microneedle may be incorporated into a surface portion of the transdermal patch. That is, for more direct or immediate delivery of the at least one *cannabis* drug into the blood stream, the one or more *cannabis* drug may be administered through a microneedle that may remain in the skin upon adhesion of the transdermal patch to a skin surface and act as a further transducer of the SAW to further optimize the advantageous effects of enhanced drug delivery and pain reduction. As shown in FIG. 10, a transdermal patch 600 comprises therapeutically effective amount of a drug 700 in a reservoir (not shown), with an actuator 400 positioned thereon to provide effective transmission of ultrasonic waves from a transducer (not shown) comprised in the actuator 400 to the tissue (i.e., skin surface). As in other embodiments, the transdermal patch comprises an adhesive surface 620 for attachment to a skin surface. Additionally, a microneedle 800 is provided through the adhesive surface 620 to provide direct transdermal administration of the drug 700 permeating into and through the microneedle 800 from the reservoir upon application of ultrasonic waves.

In yet another embodiment of the invention, FIG. 11 shows an actuator 400 comprised on a surface of a separate portable or hand-held controller 900, rather than incorporated into the transdermal patch 600. A selective interface 950 is provided between a surface portion of the reservoir (not shown) comprising the therapeutic agent or drug, i.e., drug layer 700, and the actuator 400, such that the hand-held controller 900 can be positioned and so as to stimulate and improve permeation of the at least one therapeutic agent or drug of the drug layer 700 from the transdermal patch 600 to a subject's skin. In such embodiments, actuator 400 may be comprised of a metallic layer and a piezoelectric layer with an electrode thereon, with the metallic layer being positioned outward such that it comes into contact with the skin. A processor (not shown) and a battery can be placed within a handle of the hand-held controller, with the actuator 400 being electrically connected thereto.

IV. Treatment Methods

Several beneficial effects have been reported from contact ultrasound physiotherapy, including local improvement of blood circulation, heating of the tissue, accelerated enzyme activity, muscle relaxation, pain reduction, and enhancement of natural healing processes. However, despite the above beneficial effects, current techniques of medical physiotherapy using ultrasonic waves are limited by the necessity of providing a direct contact interface between the ultrasonic transducer and the tissue in order to maintain an effective transmission of the ultrasonic waves from the transducer to the tissue. This requirement makes ultrasound treatments unsuitable for many applications, including, e.g., treatment of fresh or open wounds.

In methods of the invention once a pharmaceutical composition comprising a therapeutically effective amount of a *cannabis* drug (and optionally one or more additional drug (s)) is provided, the therapeutically effective amount of the *cannabis* drug is topically administered to a skin surface of a subject for transdermal absorption by, for example, iontophoresis, phonophoresis, or microneedle technologies, and/or by applying the cannabinoid as a topical cream, salve, ointment or other topical formulation, and/or by using the transdermal patch described herein.

Embodiments of the invention provide for SAW-generating electrically driven methods for more effective or enhanced drug delivery. These methods may further treat or alleviate symptoms associated with a disease or condition of a patient. Provided in embodiments of the invention are methods for improved drug delivery, such methods generally comprising: topically applying a pharmaceutical composition comprising a therapeutically effective amount of at least one drug to a skin surface of a subject; and applying surface acoustic waves (SAW) on the skin surface such that a distance between two maximal amplitudes of bending vibrations is proportional to a half wave length of the SAW applied on the skin surface; and controlling application of the SAW so as to achieve desired effects of improved delivery and transdermal absorption of the therapeutically effective amount of the at least one drug to the subject in need thereof.

Generally speaking, transdermal delivery involves contacting the cannabinoid composition with the subject's skin under conditions effective for at least one of the provided *cannabis* drugs to penetrate the skin. In an illustrative embodiment of the invention, the transdermal patch is configured to control the uniform release of the *cannabis* drug over a period of time. In practice, the transdermal patch of the invention, which includes the *cannabis* drug in a pharmaceutical composition, is positioned on the subject's skin under conditions effective to transdermally deliver the selected *cannabis* drug in a therapeutically effective amount to the subject's skin for transdermal absorption. Such conditions can include, for example, positioning the transdermal patch on a portion of the subject's skin and/or orienting the transdermal patch on the subject's skin such that the cannabinoid, when released from the transdermal patch, contacts the subject's skin.

The application of a pharmaceutical composition in methods of the invention comprises applying a transdermal patch to a skin surface, wherein the transdermal patch comprises the pharmaceutical composition in a reservoir and is configured to effectuate a desired rate of administration of the at least one *cannabis* drug to the skin surface. Specifically, the transdermal patch comprises: a reservoir holding a pharmaceutical composition comprising a therapeutically effective amount of the at least one *cannabis* drug; an adhesive layer covering at least an outer perimeter of an outer surface of the transdermal patch, the outer surface being a surface facing away from the reservoir within the transdermal patch; an impermeable layer forming a protective surface of impermeable material over the transdermal patch; and a removable protective layer over the adhesive layer. In preferred embodiments, the transdermal patch further comprises an actuator of the transducer, wherein the actuator is electronically connected via a cable to a separate energy generating unit configured to transmit energy to the actuator upon activation. In an active state, the energy generating unit transmits energy to the actuator based on a user's selection of power output and/or treatment cycle on a display portion of the energy generating unit.

The transdermal patch further comprises an actuator comprising an electromagnetic transducer. The actuator is electronically connected with a cable to a separate energy generating unit configured to transmit energy to the actuator upon activation. In an active state, the energy generating unit transmits energy to the actuator based on a user's selection of power output and/or treatment cycle. The transducer is preferably disposed on the transdermal patch so as to be in contact with a skin surface upon adhesion of the transdermal patch to the skin surface.

As a general concept of the various embodiments of the invention, a pharmaceutical composition comprising at least one drug in an amount therapeutically effective for treating or alleviating symptoms of a condition or disease of a subject is comprised within a transdermal patch. Specific configurations of the transdermal patch encompassed by the present invention may vary, including with respect to the pharmaceutical compositions, the arrangement of the pharmaceutical composition(s) within the transdermal patch (e.g., within a drug-in adhesive layer, a cavity, and/or one or more polymeric matrix layer(s)), the presence of optional microporous rate-controlling membrane(s), and the type of actuator in terms of the transducer used, as well as the location or arrangement of the actuator(s) within the transdermal patch. The actuator of the transdermal patch is operably connected to a processor of a portable energy/ultrasound-generating unit. In embodiments, the actuator is electrically connected to the processor by a bus. Upon activation of the energy-generating unit, a driving signal electrically communicated by the process causes substantial vibration of the actuator(s) to generate and emit the desired SAW effect through the transdermal patch (including to effectuate drug delivery from the transdermal patch) and on the skin surface in contact with and around the transdermal patch.

Provided are various methods of using the portable ultrasound system as described herein to apply ultrasonic energy to a subject (human or animal) at a target area, preferably the skin. In preferred embodiments, the methods of the invention use the portable ultrasound system described herein, which comprises: an energy generating unit operative to generate a driving signal that can be transformed into ultrasonic energy by a transducer, wherein the energy generating unit at least comprises a power source, a controller, an oscillator, and a modulator; and an actuator comprised of an electromagnetic transducer, a base portion, an activating portion, and a processor.

In embodiments, the processor comprises a controller for controlling output parameters of the processor. The controller is in electrical communication with an oscillator for providing signals at various frequencies, a modulator for modulating parameters such as frequency, amplitude, etc., and a vibration method selector for providing different types of vibrations, such as single-phase, two-phase or multiphase vibrations.

In general terms, the ultrasound transducer is configured to receive an energy signal from the energy generating unit and to transform the energy signal into ultrasonic energy. The transducer also controls the direction of the ultrasonic energy emitted based on the positioning/placement of the transducer.

The selected signal of the selected vibration type is sent through an amplifier to the actuator. In embodiments where electrical signals are sent from actuator to processor, the signals are received by a receiver within the processor. In some instances, signals may be sent by a separate sensor placed on or near or incorporated within the actuator. Signals received by receiver are sent to a memory module where they are compared with expected values. Results of the comparison are then either sent to the controller, where signal parameters (such as amplitude and frequency) may be automatically adjusted based on information received, or sent to an alarm for alerting a user that parameters should be adjusted manually.

Penetration depths of SAW may be controlled through wavelength, which depends on frequency. When SAW has a relatively long wavelength, deep penetration is achieved in comparison to SAW with short wavelengths as energy intensity decreases with increased distance from the surface. The propagation of SAW depends on density, elasticity, and other material properties of the solid, such as, e.g., the skin, and the SAW is influenced a great deal by the selected frequency and material thickness. With Lamb waves in particular, a number of modes of particle vibration are possible, but the two most common are symmetrical and anti-symmetrical. The complex motion of the particles is similar to the elliptical orbits for surface waves. The presence of SAW on internal and external surfaces of skin causes a pushing/pulling effect of materials on these surfaces, including fluids and particulates suspended therein. There are several methods for producing SAW on skin, including electromagnetic, laser pulses, or piezoelectric methods, as discussed herein.

In preferred embodiments, the actuator is a piezoelectric actuator that works by converting electrical signals from the processor to mechanical energy, with the mechanical energy then being transmitted to skin and creating SAW on surfaces thereof. In some embodiments, the actuator is configured to transmit electrical signals proportional to the mechanical energy created by the processor, and thus may provide a feedback loop to regulate the electrical signals produced by the processor. The transdermal patch may comprise multiple actuators. In such embodiments the propagation of running SAW in various directions can result in standing waves in an area where the waves overlap, which results in a more focused acoustic energy treatment in that area. In some embodiments the actuator may be ring-shaped, or multiple actuators may be circularly arranged. This configuration provides for standing waves to be created in the central portion thus concentrating acoustic pressure and creating a micro-cavitation effect. The cavitation typically also leads to a significant increase in temperature. Therefore, embodiments of the invention where the circular arrangement or construction of the actuator(s) is preferred include conditions where high energy may be therapeutically useful.

In some embodiments, the SW may be combined with conventional ultrasound and/or further enhanced by addition of a laser beam. In some embodiments, conventional ultrasound is continuous, and in other embodiments the conventional ultrasound is pulsed. The laser therapy may include a pulsed, scanned or gated laser continuous wave laser or incoherent radiation of ultraviolet therapy. The combination of SAW, conventional ultrasonic waves, laser beams and energized medicines (highly activated by ultrasonic waves and laser beams) should e.g., destroy the surface bacteria and result in a higher level of disinfection by the energized pharmaceutical composition of the transdermal patch than.

Additional actuators suitable for use in embodiments of the invention may include those disclosed in U.S. Patent Application Publications Nos. 2005/0268921, 2005/0095351, and 2005/0038376, all of which are incorporated by reference herein in their entireties.

In addition to improving transdermal administration and absorption of drugs, it is also an object of the present invention to provide methods of treating a disease or condition, or symptoms associated therewith, in a human subject by using a portable ultrasound system with a transdermal patch as described herein. By virtue of the methods of treatment described herein, the disease state/condition to be treated may be treated much faster and more effectively than by conventional administration methods. Prophylaxis of various diseases or symptoms associated therewith may also be achieved as a result of the treatment methods described herein.

The topical pharmaceutical composition provided for use in embodiments of the invention comprises a drug in an amount which is therapeutically effective when administered topically according to embodiments of the invention, but which provides a subtherapeutic plasma concentration if administered orally. By applying the pharmaceutical composition comprising a therapeutically effective amount of at least one *cannabis* drug (and optionally one or more additional drug(s)) in combination with ultrasound waves using the portable ultrasound system described herein, it is possible to use lower doses of drug or achieve faster relief than if administered without such ultrasound, and the lower plasma levels of drug which result from the lower doses may thereby further reduce unwanted side effects of the drug.

By topically applying a therapeutically effective amount of at least one *cannabis* drug along with SAW generated by the portable ultrasound system described herein, methods of the invention are directed to relieving the symptoms of a variety of diseases, conditions, syndromes, disorders, and other forms of illness. For example, patients suffering from illnesses, such as cancer or AIDS, often experience symptoms including lack of appetite, which can be relieved by the compositions and methods of the present invention. Patients suffering from neuropathy experience chronic pain and other symptoms, which can be relieved based on the present invention. The methods of the invention can also be used to relieve symptoms of stroke, head injuries, and neurodegenerative disorders. The mechanisms by which symptoms are relieved is not particularly critical to the practice of the present invention. Illustratively, symptoms can be relieved by directly treating the underlying illness or by blocking the biological pathways by which the illness produces the symptoms. Moreover, methods of the invention can be used to relieve discomfort associated with the treatment of illness. For example, the present invention can be used to relieve nausea, vomiting and/or other discomforts associated with chemotherapy and other treatment regimens used to treat cancer and other illnesses.

In certain embodiments, by applying the formulation of the present invention comprising a dose of drug at the back of the neck at the hair-line for access to posterior cervical afferents with free nerve endings under the surface of the skin, it may be possible for the use of lower doses of drug or faster relief of headache than if applied to the trunk or limbs of a human patient, and the lower plasma levels of drug which result from lower doses may thereby reduce unwanted side effects of the drug.

In certain embodiments of the invention, the method of treating a subject comprising applying a topical formulation which comprises a *cannabis* drug and which is useful for treatment of a disease state or condition further comprises, if necessary, pre-treatment of the skin with an enhancer to increase the permeability of the skin to the applied drug. The methods of the invention may include pre-treatment or prepping of the skin area with a substance that opens up skin pores. Additionally, the methods of the invention may comprise pre-treatment or prepping of the skin with an alcohol swab or the like to rid area of dirt, oil, make-up, and the like prior to application of the drug.

In various aspects of the present invention, provided are methods for topically applying at least one *cannabis* drug to a subject in need thereof, wherein the subject in need thereof has a disease, condition, or symptoms or a disease or condition that would benefit from the at least one *cannabis* drug, the topical application comprising: applying a transdermal patch to a skin surface of the subject, wherein the transdermal patch is connected to (or otherwise connecting) the transdermal patch to the portable energy generating unit, preferably via bus coupled to the actuator; and activating the portable energy generating unit to generate surface acoustic waves, wherein a transducer comprised by actuator in the transdermal patch delivers SAW onto the skin surface. The energy of the SAW applied to the skin is effective to penetrate below the surface of the skin and is further effective to alleviate pain in tissue of the subject in and around the skin surface. According to this method, ultrasound energy is topically applied to a skin surface of the subject along with the at least one *cannabis* drug, wherein the ultrasound energy is generated by the system and is effective to penetrate deep into the tissue of the subject, thus not being limited to just providing surface ultrasound energy.

The present invention further contemplates administration of the *cannabis* drug(s) directly below the skin to affect direct uptake and stimulation of the free nerve endings under the epidermis. Such administration can be carried out as an injection (subcutaneous injection) as shown in FIG. 10 or implantation of the drug below the skin in immediate or sustained release forms. It will be appreciated by those skilled in the art that providing the drug in sustained release form and administering it in a suitable form below the skin may provide benefits, including less frequent administration (e.g., in chronic therapy).

According to the present invention, transdermal administration of at least one *cannabis* drug using the portable ultrasound system described herein results in synergistic absorption and delivery of the at least one *cannabis* drug, as compared to topical administration of the drug alone, including via the transdermal patch described herein. Although topical application of the transdermal patch comprising a therapeutically effective amount of the at least one *cannabis* drug addresses various drawbacks and complications of conventional methods for topical administration of drugs, the combined application of the drug with pulsed SAW results in greatly improved rates of administration, absorption, and delivery of the drug(s) into the bloodstream, while also providing a controlled rate of administration, improved effectiveness of the drug with reduced dosage, and synergistic pain relief compared with application of therapeutic ultrasound to skin surface according to known methods or without the at least one *cannabis* drug.

Numerous specific details are set forth in the above disclosure in order to provide a thorough understanding of the present invention. It will be understood by those of ordinary skill in the art that the present invention may be practiced without these specific details. In other instances, well-known methods, procedures, components and structures may not have been described in detail so as not to obscure the present invention. Before explaining at least one embodiment of the present invention, it is to be understood that the invention includes other embodiments and persons skilled in the art will understand that it may be practiced or carried out in various different ways. Such modifications and variations that may be apparent to persons skilled in the art are intended to be included within the scope of the invention as defined by the accompanying claims.

V. Cited References

1. Grotenhermen F., "Pharmacokinetics and pharmacodynamics of cannabinoids," *Clin. Pharmacokinet.* 42:327-60 (2003).
2. Pacifici R. et al., "Evaluation of Long-term stability of cannabinoids in standardized preparations of cannabis flowering tops and cannabis oil by ultra-high-performance liquid chromatography tandem mass spectrometry," *Clin. Chem. Lab. Med.* 56:e94-e96 (2018).
3. Stucky et al., "Mechanisms of pain," *Proc. Natl. Acad. Sci. USA* 98:11845-6 (2011).
4. Jensen et al., "The impact of neuropathic pain on health-related quality of life: Review and implications," *Neurology* 68:1178-82 (2007).
5. Finnerup et al., "The evidence for pharmacological treatment of neuropathic pain," *Pain* 150:573-81 (2010).
6. De Vries et al., "Dronabinol and chronic pain: Importance of mechanistic considerations," *Expert Opin. Pharmacother.* 15:1525-34 (2014).

7. Jensen et al., "Medical marijuana and chronic pain: A review of basis science and clinical evidence," *Current Pain Headache Rep.,* 119 (2018).

8. Guindon et al., "The endocannabinoid system and pain," *CNS Neurol. Disord. Drug Targets* 8:403-21 (2009).

9. Zhang et al., "Can modulating inflammatory response be a good strategy to treat neuropathic pain?" *Curr. Pharm. Des.* 21:831-9 (2015).

10. Kumari et al., "Biodegradable polymeric nanoparticles based drug delivery systems," *Colloids Surf Biointerfaces* 75:1-18 (2010).

11. Allen et al., "Drug Delivery Systems: Entering the Mainstream," *Science* 303:1818-22 (2004).

12. Allen et al., "Liposomal Drug Delivery Systems, From Concept to Clinical Applications," *Adv. Drug Deliv. Rev.* 65:36-48 (2013).

What is claimed is:

1. A transdermal patch, comprising:

an impermeable layer forming an upper surface of the transdermal patch;

a first drug layer comprising a first pharmaceutical composition comprising a cannabis drug and at least one pharmaceutically acceptable excipient, the cannabis drug being a cannabinoid selected from the group consisting of tetrahydrocannabinol (THC), cannabinol (CB), cannabidiol (CBD), and cannabichromene (CBC), and is present in an amount therapeutically effective for treating or alleviating acute or chronic pain associated with a disease or condition of a subject;

an adhesive layer forming at least a portion of a lower surface of the transdermal patch, the adhesive layer being configured to allow passage of the first pharmaceutical composition from the first drug layer to the skin of the subject;

a removable protective layer disposed on a lower surface of the adhesive layer;

an actuator with an integrated piezo transducer located on a lower surface of the transdermal patch such that a metal surface of the transducer faces a direction of adhesion of the transdermal patch.

2. The transdermal patch according to claim 1, further comprising a first rate-controlling microporous membrane on a lower surface of the first drug layer, thereby defining a reservoir containing the first drug layer between the impermeable layer and the rate-controlling microporous membrane, wherein the rate-controlling microporous membrane is configured to allow the first pharmaceutical composition to permeate therethrough to the subject at a controlled delivery rate.

3. The transdermal patch according to claim 2, further comprising a second drug layer comprising a second pharmaceutical composition different from the first pharmaceutical composition and being separated from the first drug layer by a second rate-controlling membrane configured to allow deliver the second pharmaceutical composition to permeate therethrough to the subject at a controlled delivery rate.

4. The transdermal patch according to claim 3, wherein each of the first pharmaceutical composition and the second pharmaceutical composition is in a transdermal dosage form selected from the group consisting of a gel, ointment, paste, cream, lotion, solution, and suspension.

5. A portable surface acoustic wave (SAW) generating system, comprising:

the transdermal patch according to claim 4; and an energy generating module operably coupled to the actuator of the transdermal patch, the energy generating module being configured to generate a driving signal when in an active state, wherein the generated driving signal causes a vibration mode of the actuator to communicate ultrasound energy to the transducer, and wherein the transducer is configured to receive, transform, and emit the ultrasound energy as SAW in a controlled direction through the transdermal patch, wherein application of the SAW through the transdermal patch results in enhanced administration and transdermal absorption of the first pharmaceutical composition and the second pharmaceutical composition in a predetermined temporal pattern and at optimum rates comprising a delayed onset of a therapeutic effect of the second pharmaceutical composition.

6. The transdermal patch according to claim 2, wherein the adhesive layer is disposed around a periphery of the lower surface of the transdermal patch, such that the first rate-controlling microporous membrane constitutes a central portion of the lower surface of the transdermal patch that is configured to contact the skin of the subject.

7. The transdermal patch according to claim 2, wherein the adhesive layer is provided across the lower surface of the transdermal patch and is configured to allow the first pharmaceutical composition to pass therethrough.

8. The transdermal patch according to claim 1, wherein the cannabis drug of the first pharmaceutical composition comprises CBD.

9. The transdermal patch according to claim 8, wherein the first pharmaceutical composition further comprises at least one therapeutic agent different from the cannabis drug, the at least one therapeutic agent being selected from a group consisting of an analgesic and an anti-inflammatory.

10. A portable surface acoustic wave (SAW) generating system, comprising: the transdermal patch according to claim 8; and an energy generating module operably coupled to the actuator of the transdermal patch, the energy generating module being configured to generate a driving signal when in an active state, the driving signal causing a vibration mode of the actuator to communicate ultrasound energy to the transducer, wherein the transducer is configured to receive, transform, and emit the ultrasound energy as SAW in a controlled direction through the transdermal patch, wherein application of the SAW through the transdermal patch results in enhanced administration and transdermal absorption of the first pharmaceutical composition.

11. A portable surface acoustic wave (SAW) generating system, comprising: the transdermal patch according to claim 1, and an energy generating module operably coupled to the actuator of the transdermal patch, the energy generating module being configured to generate a driving signal when in an active state, wherein the generated driving signal causes a vibration mode of the actuator to communicate ultrasound energy to the transducer, and wherein the transducer is configured to receive, transform, and emit the ultrasound energy as SAW in a controlled direction through the transdermal patch, wherein application of the SAW through the transdermal patch results in enhanced administration and transdermal absorption of the first pharmaceutical composition from the transdermal patch.

12. The portable SAW generating system according to claim 11, wherein the energy generating module is a portable handheld device comprising a power source, a controller, an oscillator, and a processor; and wherein the cannabis drug of the first pharmaceutical composition comprises CBD.

13. The portable SAW generating system according to claim 12, comprising two or more of the transdermal patches, the two or more transdermal patches being connected to a single processor or to two or more processors of the energy generating module.

14. The transdermal patch according to claim 1, wherein the integrated piezo transducer has a profile height of 6 mm or less.

* * * * *